(12) United States Patent
Low et al.

(10) Patent No.: US 7,740,854 B2
(45) Date of Patent: Jun. 22, 2010

(54) TREATMENT OF MACROPHAGE MEDIATED DISEASE

(75) Inventors: Philip S. Low, West Lafayette, IN (US); Mary Jo Turk, New York, NY (US)

(73) Assignee: Purdue Research Foundation, West Lafayette, IN (US)

( * ) Notice: Subject to any disclaimer, the term of this patent is extended or adjusted under 35 U.S.C. 154(b) by 132 days.

(21) Appl. No.: 10/138,275

(22) Filed: May 2, 2002

(65) Prior Publication Data

US 2002/0192157 A1    Dec. 19, 2002

Related U.S. Application Data

(60) Provisional application No. 60/288,208, filed on May 2, 2001.

(51) Int. Cl.
*A61K 39/00* (2006.01)
*A61K 39/38* (2006.01)
*A61K 39/385* (2006.01)

(52) U.S. Cl. ............... 424/184.1; 424/185.1; 424/193.1

(58) Field of Classification Search .............. 424/184.1, 424/193.1
See application file for complete search history.

(56) References Cited

U.S. PATENT DOCUMENTS

| | | | |
|---|---|---|---|
| 2,816,110 | A | 12/1957 | Sletzinger et al. |
| 4,713,249 | A | 12/1987 | Schroder |
| 5,057,540 | A | 10/1991 | Kensil et al. |
| 5,094,848 | A | 3/1992 | Brixner |
| 5,108,921 | A | 4/1992 | Low et al. |
| 5,140,104 | A | 8/1992 | Coughlin et al. |
| 5,266,333 | A | 11/1993 | Cady et al. |
| 5,273,965 | A | 12/1993 | Kensil et al. |
| 5,336,506 | A | 8/1994 | Josephson et al. |
| 5,373,093 | A | 12/1994 | Vallarino et al. |
| 5,399,338 | A | 3/1995 | Born et al. |
| 5,416,016 | A | 5/1995 | Low et al. |
| 5,417,982 | A | 5/1995 | Modi |
| 5,443,829 | A | 8/1995 | Kensil et al. |
| 5,508,310 | A | 4/1996 | Rhodes |
| 5,547,668 | A * | 8/1996 | Kranz et al. ............. 424/181.1 |
| 5,552,545 | A | 9/1996 | Pearce et al. |
| 5,583,112 | A | 12/1996 | Kensil et al. |
| 5,635,382 | A | 6/1997 | Low et al. |
| 5,650,398 | A | 7/1997 | Kensil et al. |
| 5,688,488 | A | 11/1997 | Low et al. |
| 5,759,546 | A | 6/1998 | Weinberg et al. |
| 5,977,081 | A | 11/1999 | Marciani |
| 6,080,725 | A | 6/2000 | Marciani |
| 6,093,382 | A | 7/2000 | Wedeking et al. |
| 6,204,371 | B1 | 3/2001 | Levinson |
| 6,231,859 | B1 | 5/2001 | Kensil |
| 6,262,029 | B1 | 7/2001 | Press et al. |
| 6,270,766 | B1 | 8/2001 | Feldman et al. |
| 6,335,434 | B1 | 1/2002 | Guzaev et al. |
| 7,033,594 | B2 | 4/2006 | Low et al. |
| 7,223,380 | B2 | 5/2007 | Yang et al. |
| 7,601,332 | B2 | 10/2009 | Vlahov et al. |
| 2001/0031252 | A1 | 10/2001 | Low et al. |
| 2002/0192157 | A1 | 12/2002 | Low et al. |
| 2003/0086900 | A1 | 5/2003 | Low et al. |
| 2003/0162234 | A1 | 8/2003 | Jallad et al. |
| 2003/0198643 | A1 | 10/2003 | Lu |
| 2004/0136910 | A1 | 7/2004 | Jallad et al. |
| 2005/0002942 | A1 | 1/2005 | Vlahov et al. |
| 2005/0164906 | A1 | 7/2005 | Riccardi |
| 2005/0244336 | A1 | 11/2005 | Low |
| 2005/0261170 | A1 | 11/2005 | Hansen et al. |
| 2006/0002891 | A1 | 1/2006 | Pouletty |
| 2006/0067946 | A1 | 3/2006 | Low et al. |
| 2006/0204565 | A1 | 9/2006 | Low et al. |
| 2007/0009434 | A1 | 1/2007 | Low et al. |
| 2007/0231266 | A1 | 10/2007 | Low et al. |
| 2007/0276231 | A1 | 11/2007 | Low et al. |

(Continued)

FOREIGN PATENT DOCUMENTS

EP    1548027    6/2005

(Continued)

OTHER PUBLICATIONS

Feldman et al Transplant. Proc. 1998, 30, 4126-4127.*

(Continued)

*Primary Examiner*—Michail A Belyavskyi
(74) *Attorney, Agent, or Firm*—Barnes & Thornburg LLP

(57) ABSTRACT

The invention relates to a method of treating or monitoring/diagnosing a disease state mediated by activated macrophages. The method comprises the step of administering to a patient suffering from a macrophage mediated disease state an effective amount of a composition comprising a conjugate or complex of the general formula $A_b$-X where the group $A_b$ comprises a ligand capable of binding to activated macrophages, and when the conjugate is being used for treatment of the disease state, the group X comprises an immunogen, a cytotoxin, or a compound capable of altering macrophage function, and when the conjugate is being used for monitoring/diagnosing the disease state, X comprises an imaging agent. The method is useful for treating a patient suffering from a disease selected from the group consisting of rheumatoid arthritis, ulcerative colitis, Crohn's disease, inflammation, infections, osteomyelitis, atherosclerosis, organ transplant rejection, pulmonary fibrosis, sarcoidosis, and systemic sclerosis.

17 Claims, 15 Drawing Sheets

U.S. PATENT DOCUMENTS

| | | | |
|---|---|---|---|
| 2008/0119475 A1 | 5/2008 | Low et al. |
| 2008/0138396 A1 | 6/2008 | Low et al. |
| 2008/0254499 A1 | 10/2008 | Low et al. |
| 2009/0012009 A1 | 1/2009 | Low et al. |
| 2009/0214636 A1 | 8/2009 | Low et al. |

FOREIGN PATENT DOCUMENTS

| | | |
|---|---|---|
| WO | WO 96/12096 | 10/1990 |
| WO | WO 94/07542 | 4/1994 |
| WO | WO 96/36367 | 11/1996 |
| WO | 97/37690 | 10/1997 |
| WO | WO 98/58678 | 12/1998 |
| WO | WO 99/41285 | 8/1999 |
| WO | 2001/19320 A2 | 3/2001 |
| WO | WO 01/39806 A1 | 6/2001 |
| WO | WO 01/74382 | 10/2001 |
| WO | WO 02/087424 | 11/2002 |
| WO | WO 03/092742 | 11/2003 |
| WO | WO 2004/100983 | 11/2004 |
| WO | WO 2004/110250 | 12/2004 |
| WO | WO 2005/069994 | 8/2005 |
| WO | WO 2006/012527 | 2/2006 |
| WO | WO 2006/101845 | 9/2006 |
| WO | WO 2008/148001 | 12/2008 |

OTHER PUBLICATIONS

Cochlovius et al., Modern Drug Discovery, 2003, pp. 33-38.*
Mestas et al J. of Immunology, 2004, 172, pp. 2731-2738.*
Van Noort et al. International Review of Cytology, 1998, v.178, pp. 127-204.*
Sudimack et al. Advanced Drug Delivery Reviews, 2000, vol. 41, pp. 147-162.*
Holmgren et al., Am J. Trop Med Hyd, 1994, 50, pp. 42-54.*
"Folate-Targeted Enzyme Prodrug Cancer Therapy Utilizing Penicillin-V Amidase and A Doxorubicin Prodrug," Lu, et al. *J. Drug Targeting* 7: 43-53 (1999).
"Selective Targeting of Malignant Cells with Cytotoxin-Folate Conjugates," Leamon, et al. *J. Drug Targeting* 2:101-112 (1994).
"Targeted Drug Delivery via the Folate Receptor," Sudimack et al. *Adv. Drug Delivery Reviews* 41: 147-162 (2000).
"Folate-Mediated Targeting of Therapeutic and Imaging Agents to Cancers," Reddy et al. *Critical Reviews in Ther. Drug Carrier Systems* 15: 587-627 (1998).
"Optimization of Folate-Conjugated Liposomal Vectors for Folate Receptor-Mediated Gene Therapy," Reddy et al. *J. Pharm. Sciences* 88: 1112-1118 (1999).
Turk, Mary Jo et al.; "Folate-targeted imaging of activated macrophages in rats with adjuvant-induced arthritis," Arthritis and Rheumatism, United States, Jul. 2002, vol. 46, No. 7, pp. 1947-1955, XP002284074.
Leamon, Christopher P. et al.; "Synthesis and biological evaluation of EC20: A new folate-derived, 99mTc-based radiopharmaceutical", Bioconjugate Chemistry, vol. 13, No. 6, pp. 1200-1210, XP002284075.
Nakashima et al., Selective Expression of Folate Receptor Beta and its Possible Role in Methotrexate Transport in Synovial Macrophages from Patients with Rheumatoid Arthritis, Arthritis Rheum. 42(8): 1609-1616 (1999).
G. Robbin Westerhof, Jan C. Schornagel, Ietje Kathmann, Ann L. Jackman, Andre Rosowsky, Ronald A. Forsch, John B. Hynes, F. Thomas Boyle, Godefridus J. Peters, Herbert M. Pinedo, and Gerrit Jansen; "Carrier-and Receptor-Mediated Transport of Folate Antagonists Targeting Folate-Dependent Enzymes: Correlates of Molecular-Structure and Biological Activity," journal article, Molecular Pharmacology, 1995, Vol. No. 48, pp. 459-471.
Eugene C. Roberts and Y. Fulmer Shealy; "Folic Acid Analogs. Modifications in the Benzene-Ring Region. 3. Neohomofolic and Neobishomofolic Acids. An Improved Synthesis of Folic Acid and Its Analogs.", journal article, Journal of Medicinal Chemistry, 1973, vol. 16, No. 6, pp. 697-699.
Eugene C. Roberts and Y. Fulmer Shealy, "Folic Acid Analogs. Modifications in the Benzene-Ring Region. 2. Thiazole Analogs," journal article, Journal of Medicinal Chemistry, 1972, vol. 15, No. 12, pp. 1310-1312.
Eugene C. Roberts and Y. Fulmer Shealy, "Folic Acid Analogs. Modifications in the Benzene-Ring Region. 1. 2'- and 3'- Azafolic Acids," journal article, Journal of Medicinal Chemistry, 1971, vol. 14, No. 2, pp. 125-130.
Louis T. Weinstock, Bernard F. Grabowski, and C. C. Cheng, "Folic Acid Analogs. II. p-{[2,6-Diamino-8-purinyl)methyl]amino}—benzoyl-L-glutamic Acid and Related Compounds," journal article, Journal of Medicinal Chemistry, 1970, vol. 13, No. 5, pp. 995-997.
Lothar Bock, George H. Miller, Klaus-J. Schaper, and Joachim K. Seydel, "Sulfonamide Structure-Activity Relationships in a Cell-Free System. 2. Proof for the Formation of a Sulfonamide-Containing Folate Analog.," journal article, Journal of Medicinal Chemistry, 1974, vol. 17, No. 1, pp. 23-28.
Eugene C. Roberts and Y. Fulmer Shealy, "Folic Acid Analogs. Modifications in the Benzene-Ring Region. 4. 3'- Ethyl—and 3'-Isopropylfolic Acids," journal article, Journal of Medicinal Chemistry, 1974, vol. 17, No. 2, pp. 219-222.
William W. Lee, Abelardo P. Martinez, and Leon Goodman, "Folic Acid Antagonists. Methotrexate Analogs Containing Spurious Amino Acids. Dichlorohomofolic Acid.", journal article, Journal of Medicinal Chemistry, 1974, vol. 17, No. 3, pp. 326-330.
Y. H. Kim, Y. Gaumont, R. L. Kisliuk, and H. G. Mautner, "Synthesis and Biological Activity of 10-Thia-10-deaza Analogs of Folic Acid, Pteroic Acid, and Related Compounds," journal article, Journal of Medicinal Chemistry, 1975, vol. 18, No. 8, pp. 776-780.
M. G. Nair and Patricia T. Campbell, "Folate Analogues Altered in the C9-N10 Bridge Region. 10-Oxafolic Acid and 10-Oxaaminopterin," journal article, Journal of Medicinal Chemistry, 1976, vol. 19, No. 6, pp. 825-829.
Laurence T. Plante, Elizabeth J. Crawford, and Morris Friedkin; "Polyglutamyl and Polylysul Derivatives of the Lysine Analogues of Folic Acid and Homofolic Acid," journal article, Journal of Medicinal Chemistry, 1976, vol. 19, No. 11, pp. 1295-1299.
John B. Hynes, Donald E. Eason, Claudia M. Garrett, and Perry L. Colvin, Jr., "Quinazolines as Inhibitors of Dihydrofolate Reductase. 4. Classical Analogues of Folic and Isofolic Acids," journal article, Journal of Medicinal Chemistry, 1977, vol. 20, No. 4, pp. 588-591.
John E. Oatis, Jr. and John B. Hynes, "Synthesis of Quinazoline Analogues of Folic Acid Modified at Position 10," journal article, Journal of Medicinal Chemistry, 1977, vol. 20, No. 11, pp. 1393-1396.
M. G. Nair, P. Colleen O'Neal, C. M. Baugh, Roy L. Kisliuk, Y. Gaumont, and Michael Rodman; "Folate Analogues Altered in the C9-N10 Bridge Region: N10-Tosylisohomofolic Acid and N10-Tosylisohomoaminopterin," journal article, Journal of Medicinal Chemistry, 1978, vol. 21, No. 7, pp. 673-677.
M. G. Nair, Shiang-Yuan Chen, Roy L. Kisliuk, Y. Gaumont, and D. Strumpf; "Folate Analogues Altered in the C9-N10 Bridge Region: 11-Thiohomofolic Acid," journal article, Journal of Medicinal Chemistry, 1979, vol. 22, No. 7, pp. 850-855.
M. G. Nair, Colleen Saunders, Shiang-Yuan Chen, Roy L. Kisliuk, and Y. Gaumont; "Folate Analogues Altered in the C9-N10 Bridge Region. 14. 11-Oxahomofolic Acid, a Potential Antitumor Agent," journal article, J. Med. Chem., 1980, vol. 23, pp. 59-65.
M. G. Nair, Timothy W. Bridges, and Timothy J. Henkel; "Folate Analogues Altered in the C9-N10 Bridge Region. 18. Synthesis and Antitumor Evaluation of 11-Oxahomoaminopterin and Related Compounds," journal article, J. Med. Chem., 1981, vol. 24, pp. 1068-1073.
Carroll Temple, Jr., L. Lee Bennett, Jr., Jerry D. Rose, Robert D. Elliott, John A. Montgomery, and John H. Mangum; "Synthesis of Psuedo Cofactor Analogues as Potential Inhibitors of the Folate Enzymes," journal article, J. Med. Chem., 1982, vol. 25, pp. 161-166.
M. G. Nair, Eldridge B. Otis, Roy L. Kisliuk, and Y. Gaumont, "Folate Analogues. 20. Synthesis and Antifolate Activity of 1, 2, 3, 4, 5, 6,—Hexahydrohomofolic Acid," journal article, J. Med. Chem., 1983, vol. 26, pp. 135-140.

M. G. Nair, David C. Salter, R. L. Kisliuk, Y. Gaumont, G. North, and F. M. Sirotnak; "Folate Analogues. 21. Synthesis and Antifolate and Antitumor Activities of N10- (Cyanomethyl)-5,8-dideazafolic Acid," journal article, J. Med. Chem., 1983, vol. 26, pp. 605-607.

M. G. Nair, Otha C. Salter, Roy L. Kisliuk, Y. Gaumont, and G. North; "Folate Analogues. 22. Synthesis and Biological Evaluation of Two Analogues of Dihydrofolic Acid Processing a 7,8- Dihydro-8-oxapterin Ring System," journal article, J. Med. Chem., 1983, vol. 26, pp. 1164-1168.

Matsuyama, T., et al., "Clinical significance of the folate receptor beta expression in rheumatoid synovial macrophages," Rheumatoid, Japan, Japan College of Rheumatology, 2001, vol. 41, No. 2, p. 265.

Gotoh, M., "Causes and treatment of rheumatoid arthritis; recent trend I. Progress in pathogenesis of rheumatoid arthritis; role of macrophages and dendritic cells," Pharma Medica, Japan, Medical Review Co., Ltd., Tokyo, 1999, vol. 17, No. 10, pp. 35-39.

Matsuyama, T., et al., "Activation and pathological significance of macrophages in rheumatoid synovitis," Clinical Immunity, Japan, Kagaku Hyoronsha, Tokyo, 1998, vol. 30, No. 2, pp. 214-219.

Mukasa, A., et al., "Function analysis of folate receptor-β in a RA synovial membrane macrophage cell line," Rheumatoid, Japan, Japan College of Rheumatology, 2000, vol. 40, No. 2, p. 378. Translation Document.

"Macrophages" from Wikipedia.

Karsten, M., and J. Roos, "Towards Usage-Based Accounting: Applying Policy-Based Intelligent Agents", ITC 15. Elsevier Science B.V., pp. 633-642 (1997).

Thomas F. Budinger et al., "New Approaches to Targeting Arthritis with Radiopharmaceuticals," The Journal of Rheumatology 1995, pp. 62-67, vol. 22:1 Supplement.

Susan Wang et al., "Synthesis, Purification, and Tumor Cell Uptake of Ga-Deferoxamine-Folate, a Potential Radiopharmaceutical for Tumor Imaging," American Chemical Society 1996, Bioconjugate Chem, pp. 56-62, vol. 7, No. 1 1996.

Reddy J.A. et al., "Folate receptor specific anti-tumor activity of folate-mitomycin conjugates," *Cancer Chemother Pharmacol.*, 2006; 58(2):229-36.

Turk M.J. et al., "Folate-conjugated liposomes preferentially target macrophages associated with ovarian carcinoma," *Cancer Letters*, 213, pp. 165-172 (2004).

Kennedy M.D. et al., "Evaluation of Folate Conjugate Uptake and Transport by the Choroid Plexus of Mice", *Pharmaceutical Research*, vol. 20(5); 714-719 (2003).

Kalgutkar A.S. et al., "Ester and Amide Derivatives of the Nonsteroidal Antiinflammatory Drug, Indomethacin, as Selective Cyclooxygenase-2 Inhibitors", *J. Med. Chem.* 2000, 43, pp. 2860-2870.

Leamon C.P. et al., "Folate-Liposome-Mediated Antisense Oligodeoxynucleotide Targeting to Cancer Cells: Evaluation in Vitro and in Vivo," *Bioconjugate Chem.*, 2003, 14, pp. 738-747.

Leamon C.P. et al., "Cytotoxicity of Momordin-Folate Conjugates in Cultured Human Cells," *The Journal of Biological Chemistry*, vol. 267, No. 35, pp. 24966-24971 (1992).

Weber C. et al., "Differential chemokine receptor expression and function in human monocyte subpopulations," *Journal of Leukocyte Biology*, vol. 67, 699-704 (2000).

Ziegler-Heitbrock H.W.L., "Definition of human blood monocytes," *Journal of Luekocyte Biology*, vol. 67, pp. 603-606 (2000).

Cairns A.P. et al., "Reduced expression of CD44 on monocytes and neutrophils in systemic lupus erythematosus: relations with apoptotic neutrophils and disease activity," Ann. Rheum. Dis., vol. 60, pp. 950-955 (2001).

U.S. Appl. No. 60/590,580, filed Jul. 23, 2004, Vlahov et al.

Baidoo K.E. et al., "High-Affinity No-Carrier-Added $^{99m}$Tc-Labeled Chemotactic Peptides for Studies of Inflammation in Vivo", Bioconj. Chem., vol. 9, pp. 208-217 (1998).

Antohe F. et al., "Increased uptake of folate conjugates by activated macrophages in experimental hyperlipemia," Cell Tiss. Res., vol. 320, pp. 277-285 (2005).

Zarev P.V. et al., "Comparative Study of Monocyte Enumeration by Flow Cytometry: Improved Detection by Combining Monocyte-Related Antibodies with Anti-CD163", Laboratory Hematology, vol. 10, 2004, pp. 24-31.

Moller B. et al., "Folinic acid antagonizes methotrexate-induced differentiation of monocyte progenitors," Rheumatol Int., vol. 22, pp. 60-67 (2002).

Dong B. et al, "2-5A-dependent RNase Molecules Dimerize during Activation by 2-5A," Journal of Bio. Chem, vol. 270, No. 8, pp. 4133-4137 (1995).

Rheumatoid Arthritis (RA), The Merck Manuals Online Medical Library, [online], Whitehouse Station, NJ: Merck Research Laboratories, 2006-2007, [retrieved on Oct. 9, 2007], available at: http://www.merck.com/mmpe/print/sec04/ch034/ch034b.html, pp. 1-9.

Wang S. et al., "Synthesis, purification, and tumor cell uptake of 67Ga-deferoxamine—folate, a potential radiopharmaceutical for tumor imaging," Bioconjugate Chem., 1996;7(1):56-62.

Barrera P. et al., "Synovial macrophage depletion with clodronate-containing liposomes in rheumatoid arthritis," Arthritis and Rheumatism, 2000, 43, pp. 1951-1959.

U.S. Appl. No. 61/235,220, filed Aug. 19, 2009, Low et al.
U.S. Appl. No. 61/157,847, filed Mar. 5, 2009, Low et al.
U.S. Appl. No. 12/526,096, filed Aug. 6, 2009, Low et al.

Nagayoshi R. et al., "Effectiveness of anti-folate receptor β antibody conjugated with truncated *Pseudomonoas exotoxin* in the targeting of rheumatoid arthritis synovial macrophages," Arthritis and Rheumatism, 2005, 52, pp. 2666-2675.

Henne W.A. et al., "Synthesis and Activity of a Folate Peptide Camptothecin Prodrug," *Bioorganic & Medicinal Chemistry Letters*, 2006, vol. 16, pp. 5350-5355.

Chensue S.W. et al., "Biologic and Immunohistochemical Analysis of Macrophage Interleukin-1α,-1β, and Tumor Necrosis Factor Production During the Peritoneal Exudative Response," *Journal of Leukocyte Biology*, 1989, vol. 46, pp. 529-537.

Ribatti D., "The Discovery of Endothelial Progenitor Cells An Historical Review," *Leukemia Research*, 2007, vol. 31, pp. 439-444.

Shibuya M., "Differential Roles of Vascular Endothelial Growth Factor Receptor-1 and Receptor-2 in Angiogenesis," *J. Biochemistry and Molecular Biology*, 2006, vol. 39, No. 5, pp. 469-478.

Shmelkov S.V. et al., "AC133/CD133/Prominin-1," *International Journal of Biochemistry & Cell Biology*, 2005, vol. 37, pp. 715-719.

Blankenberg F. et al., "Radionuclide imaging of post-ischemic inflammation using radiolabeled monocyte chemotactic peptide (MCP-1) and annexin V," *J. of Nuclear Medicine*, 43 Suppl, p. 110P, May 2002 (abstract).

Hilgenbrink A. et al., "Folate Receptor-Mediated Drug Targeting: From Therapeutics to Diagnostics," *J. of Pharmaceutical Sciences*, 94, pp. 2135-2146 (2005).

U.S. Appl. No. 12/301,864, filed Nov. 21, 2008, Low et al.
U.S. Appl. No. 61/154,694, filed Feb. 23, 2009, Low.

Claassen E. et al., "Preparation and characteristics of dichloromethylene diphosphonate-containing liposomes," *J. Microencapsul.*, 1986, 3, pp. 109-114.

Paulos et al., "Folate-targeted immunotherapy effectively treats established adjuvant and collagen-induced arthritis," *Arthritis Res. Ther.*, 2006, 8, R77.

Van Eden W. et al., "(Altered) self peptides and the regulation of self reactivity in the peripheral T cell pool," *Immunol Rev.*, 1996, 149, pp. 55-73.

Fletcher D.S. et al., "Therapeutic administration of a selective inhibitor of nitric oxide synthase does not ameliorate the chronic inflammation and tissue damage associated with adjuvant-induced arthritis in rats," *J. Pharmacol. Exp. Titer.*, 284, pp. 714-721 (1998).

Kindt T.J. et al., "Phagocytosis is followed by digestion and presentation of antigen", Kuby immunology 6th ed., W.H. Freeman and Company, 2007, pp. 36-37.

Carpenter et al., "Characterization of the binding of 125-I-labeled epidermal growth factor to human fibroblasts", J Biol. Chem., 1975; 250(11): 4297-4304.

Dubaniewicz A. et al., "Apoptosis mononuclear cells in sarcoidosis," Pol Merkur Lekarski, 2005; 19(112):563-6 (abstract only).

Hodge G et al., "Up-regulation of interleukin-8, interleukin-10, monocyte chemotactic protein-1, and monocyte chemotactic protein-3 in peripheral blood monocytes in stable lung transplant recipients: are immunosuppression regimens working?," Transplantation, 2005; 79(4):387-91 (abstract only).

Du M. et al, "VEGF gene expression is regulated post-transcriptionally in macrophages," FEBS J., 2006;273(4):732-45 (abstract only).

Hanauer S.B., "Inflammatory bowel disease: epidemiology, pathogenesis, and therapeutic opportunities," Inflamm Bowel Dis., 2006; 12 Suppl 1:S3-9 (abstract only).

Hasegawa M. et al., "Up regulated expression of fractalkine/CX3CL1 and CX3CR1 in patients with systemic sclerosis," Ann Rheum Dis., 2005; 64(1):21-8 (abstract only).

Belperio J.A. et al., "The role of the Th2 CC chemokine ligand CCL17 in pulmonary fibrosis," J Immunol., 2004; 173(7):4692-8 (abstract only).

Moalem G. et al., "Immune and inflammatory mechanisms in neuropathic pain," Brain Res Rev., 2006; 51(2):240-64 (abstract only).

Zenz R. et al., "Psoriasis-like skin disease and arthritis caused by inducible epidermal deletion of Jun proteins," Nature, 2005; 437(7057):369-75 (abstract only).

Tazi A. et al., "Spontaneous release of granulocyte colony-stimulating factor (G-CSF) by alveolar macrophages in the course of bacterial pneumonia and sarcoidosis: endotoxin-dependent and endotoxin-independent G-CSF release by cells recovered by bronchoalveolar lavage," Am J Respir Cell Mol Biol., 1991; 4(2):140-7 (abstract only).

Fattal-German M. et al., "Expression of intercellular adhesion molecule 1 (ICAM-1) on human alveolar macrophages," Ann Pharm Fr., 1995; 53(3):97-110 (abstract only).

Aramaki Y., "Liposomes as immunomodulator—inhibitory effect of liposomes on NO production from macrophages," Biol Pharm Bull., 2000; 23(11):1267-74 (abstract only).

Rogler G. et al., "T-cell co-stimulatory molecules are upregulated on intestinal macrophages from inflammatory bowel disease mucosa," Eur J Gastroenterol Hepatol., Oct. 1999; 11(10):1105-11 (abstract only).

Pantelidis P. et al., "Up-regulation of IL-8 secretion by alveolar macrophages from patients with fibrosing alveolitis: a subpopulation analysis," Clin Exp Immunol., 1997; 108(1):95-104 (abstract only).

Carre P. et al., "Cytokines and pulmonary fibroses," Rev Mal Respir., 1993; 10(3):193-207 (abstract only).

Bar-Or A. et al., "Molecular pathogenesis of multiple sclerosis," J Neuroimmunol., 1999; 100(1-2):252-9 (abstract only).

Goebeler M. et al., "The C-X-C chemokine Mig is highly expressed in the papillae of psoriatic lesions," J Pathol., 1998; 184(1):89-95 (abstract only).

Rodenburg R.J. et al., "Superinduction of interleukin 8 mRNA in activated monocyte derived macrophages from rheumatoid arthritis patients," Ann Rheum Dis., 1999; 58(10):648-52 (abstract only).

Bohm E. et al., "What's new in exogenous osteomyelitis?," Pathol Res Pract., 1992; 188(1-2):254-8 (abstract only).

Okopien B. et al., "Monocyte suppressing action of fenofibrate," Pharmacol Rep., 2005; 57(3):367-72 (abstract only).

Chung F.M. et al., "Peripheral total and differential leukocyte count in diabetic nephropathy: the relationship of plasma leptin to leukocytosis," Diabetes Care, 2005; 28(7):1710-7 (abstract only).

Wun T. et al., "Activated monocytes and platelet-monocyte aggregates in patients with sickle cell disease," Clin Lab Haematol., 2002; 24(2):81-8 (abstract only).

Dichamp I. et al., "Increased nuclear factor-kappaB activation in peripheral blood monocytes of patients with rheumatoid arthritis is mediated primarily by tumor necrosis factor-alpha," J Rheumatol., 2007; 34(10):1976-83 (abstract only).

Yamane K. et al., "Monocyte-mediated suppression of T lymphocyte blastogenesis and its reversal by deoxyguanosine. Defects in patients with systemic lupus erythematosus," Int Arch Allergy Appl Immunol., 1986; 80(2):132-8 (abstract only).

Okamoto II. et al., "Human monocyte-derived multinucleated giant cells," Nihon Ilansenbyo Gakkai Zasshi, 2004;73(3):245-51 (abstract only).

Harrison's Principles of Internal Medicine, selected passages, 1998, p. 3, 7, 10.

\* cited by examiner

Increased uptake of folate-targeted imaging agent was seen in patient with inflamed joint Fig. 8 Folate-linked chelator EC20

TREATMENT OF MACROPHAGE MEDIATED DISEASE

CROSS REFERENCE TO RELATED APPLICATIONS

This application claims priority under 35 U.S.C §119(e) to U.S. Provisional Application Ser. No. 60/288,208, filed on May 2, 2001.

FIELD OF THE INVENTION

This invention relates to methods for treating and monitoring disease states mediated by activated macrophages. More particularly, ligands that bind to activated macrophages are complexed with an imaging agent, or an immunogen, a cytotoxin or an agent for altering macrophage function for administration to a diseased host for diagnosis and/or treatment of macrophage mediated disease.

BACKGROUND AND SUMMARY OF THE INVENTION

The mammalian immune system provides a means for the recognition and elimination of foreign pathogens. While the immune system normally provides a line of defense against foreign pathogens, there are many instances where the immune response itself is involved in the progression of disease. Exemplary of diseases caused or worsened by the host's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease often resulting in organ transplant rejection.

Macrophages are generally the first cells to encounter foreign pathogens, and accordingly, they play an important role in the immune response. However, activated macrophages can contribute to the pathophysiology of disease in some instances. Activated macrophages nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response.

Rheumatoid arthritis (RA) is a systemic disease characterized by chronic inflammatory synovitis, usually involving peripheral joints. The synovial inflammation causes cartilage deterioration and bone erosion with consequent destruction of joint integrity. Rheumatoid factors, which are autoantibodies reactive with the Fc region of IgG, are found in more than two-thirds of patients with RA indicating that RA has an autoimmune component.

RA is seen throughout the world in as much as 2% of the population, with 80% of RA patients developing the disease between the ages of 35 and 50. The clinical manifestations of RA include pain, swelling, and tenderness in the joints resulting in limitation of motion, weakness, fatigue, and weight loss. RA is a systemic disease and, consequently, has extra-articular manifestations, especially in patients with high titers of rheumatoid factors. These symptoms include rheumatoid nodules with an inner zone of necrotic material, a mid-zone of macrophages, and an outer zone of granulated tissue, muscle atrophy, osteoporosis, pulmonary fibrosis, and rheumatoid vasculitis which may result in cutaneous ulceration, digital gangrene, or neurovascular disease.

Rheumatoid synovitis, characteristic of RA, results in an increase in the number of synovial lining cells, hyperplasia and hypertrophy of the synovial lining cells, microvascular injury, edema, and infiltration of cells such as T cells, macrophages, and dendritic cells. The rheumatoid synovium is characterized by the presence of secreted products of immune cells such as factors secreted by T lymphocytes including IL-2, IFN-δ, IL-6, IL-10, GM-CSF and TGFα and β and factors secreted by activated macrophages including IL-1, IL-6, IL-8, IL-10, GM-CSF, macrophage CSF, and TGFβ. The production of these cytokines appears to account for much of the pathology of RA including inflammation of the synovium, synovial cell proliferation, cartilage and bone deterioration, and systemic symptoms of the disease.

RA may be treated using various therapies including physical therapy, rest, and splinting. Therapeutic agents are also used for the treatment of RA including aspirin and nonsteroidal anti-inflammatory drugs to control local inflammation. However, these agents have a minimal effect on the progression of the disease and are associated with toxic side effects. Disease-modifying anti-rheumatic drugs, such as α-penicillamine and sulfasalazine, are also used to treat RA, but the benefit from these drugs is delayed for weeks or months and these drugs have toxic side effects. Immunosuppressive and cytotoxic drugs suppress symptoms of RA in some patients, but are associated with toxicity. Intra-articular glucocorticoids have also been used, but provide only transient relief. Accordingly, there is a need for the development of new therapies with reduced toxicity that are efficacious for the treatment of RA and other diseases caused or worsened by activated macrophages.

The folate receptor (FR) is a 38 KDa GPI-anchored protein that binds the vitamin folic acid with high affinity (<1 nM). Following receptor binding, rapid endocytosis delivers the vitamin into the cell, where it is unloaded in an endosomal compartment at low pH. Importantly, covalent conjugation of small molecules, proteins, and even liposomes to folic acid does not alter the vitamin's ability to bind the folate receptor, and therefore, folate-drug conjugates can readily enter cells by receptor-mediated endocytosis.

Because most cells use an unrelated reduced folate carrier (RFC) to acquire the necessary folic acid, expression of the folate receptor is restricted to a few cell types. With the exception of kidney and placenta, normal tissues express low or nondetectable levels of FR. However, many malignant tissues, including ovarian, breast, bronchial, and brain cancers express significantly elevated levels of the receptor. In fact, it is estimated that 95% of all ovarian carcinomas overexpress the folate receptor. It has recently been reported that FRβ, the nonepithelial isoform of the folate receptor, is expressed on activated (but not resting) synovial macrophages. Thus, Applicants have attempted to utilize folate-linked compounds potentially capable of altering the function of activated macrophages, to treat macrophage-mediated disease states. For example, Applicants have found that folate-linked immunogens can be used to redirect the host immune response in arthritic animals to activated macrophages at the site of inflammation to deplete macrophages and reduce arthritic inflammation.

Scintigraphic imaging agents are a million times more sensitive than magnetic resonance imaging (MRI) contrast agents, and their selectivity can be enhanced by their targeting to lesion-specific cell markers. Indeed, the radioisotope $^{99m}Tc$ has been delivered to arthritic tissues using nonspecific IgG, anti-CD4 antibodies, CD11b/CD14-glycolipopeptide ligands, and E-selectin binding peptides. Preclinical studies with such radioimaging agents have clearly emphasized the value of imaging arthritic tissues in-vivo, however, the selectively of the current imaging agents is not yet optimal, and none of the present compounds is targeted exclusively to activated macrophages. In view of the emergence of folate receptor activity during macrophage activation, Applicants have undertaken to determine whether a folate-targeted $^{99m}$Tc imaging agent might be used to image arthritic lesions in vivo.

To determine whether expression of this high affinity FR might be exploited to selectively target drugs to activated macrophages at sites of inflammation, folic acid has been conjugated to a $^{99m}$Tc chelator, and its distribution evaluated in both normal and diseased tissues of rats with adjuvant-induced arthritis. The folate-linked $^{99m}$Tc chelate complex, termed EC20, was indeed found to concentrate in the arthritic extremities of diseased rats, but not in the joints of healthy rats. The intensity of the gamma scintigraphic images of affected tissues was found to be greatly reduced in the presence of excess competing folic acid. Furthermore, liver and spleen of arthritic animals also showed enhanced uptake of EC20 and increased levels of FR, confirming that systemic activation of macrophages accompanies adjuvant-induced arthritis. Depletion of macrophages from arthritic animals reduced tissue FR content and concomitantly abolished uptake of EC20. Furthermore, Kupffer cells isolated from rats with adjuvant-induced arthritis exhibited a significantly higher binding capacity for folate conjugates than Kupffer cells from healthy rats. Thus, Applicants have found that EC20 is useful for assaying the participation of activated macrophages in inflammatory pathologies such as rheumatoid arthritis.

The present invention is directed to a method for treating and monitoring disease states mediated by activated macrophages. In accordance with one embodiment of the present invention, disease states mediated by activated macrophages are treated by redirecting host immune responses to activated macrophages or by altering the function of activated macrophages or by direct killing of activated macrophages. In one aspect of the invention, to promote killing of activated macrophages, ligands that bind specifically to activated macrophages are conjugated with an immunogen to redirect host immune responses to the activated macrophage population, or they are conjugated to a cytotoxin for direct killing of macrophages. Ligands that can be used in the conjugates of the present invention include those that bind to receptors expressed specifically on activated macrophages, such as the folate receptor, or ligands such as monoclonal antibodies directed to cell surface markers specifically expressed on activated macrophages. In another aspect of the invention ligands that bind specifically to activated macrophages are conjugated with an imaging agent; the conjugate is administered to a patient for diagnosing and monitoring the progression of diseases mediated by activated macrophages.

In one embodiment, a method of treating or monitoring/diagnosing a disease state mediated by activated macrophages is provided. The method comprises the step of administering to a patient suffering from a macrophage mediated disease state an effective amount of a composition comprising a conjugate or complex of the general formula $A_b$-X, where the group $A_b$ comprises a ligand capable of binding to activated macrophages, and when the conjugate is being used for treatment of the disease state, the group X comprises an immunogen, a cytotoxin, or a compound capable of altering macrophage function, and when the conjugate is being used for monitoring/diagnosing the disease state, X comprises an imaging agent.

DETAILED DESCRIPTION OF THE INVENTION

Figure 1:
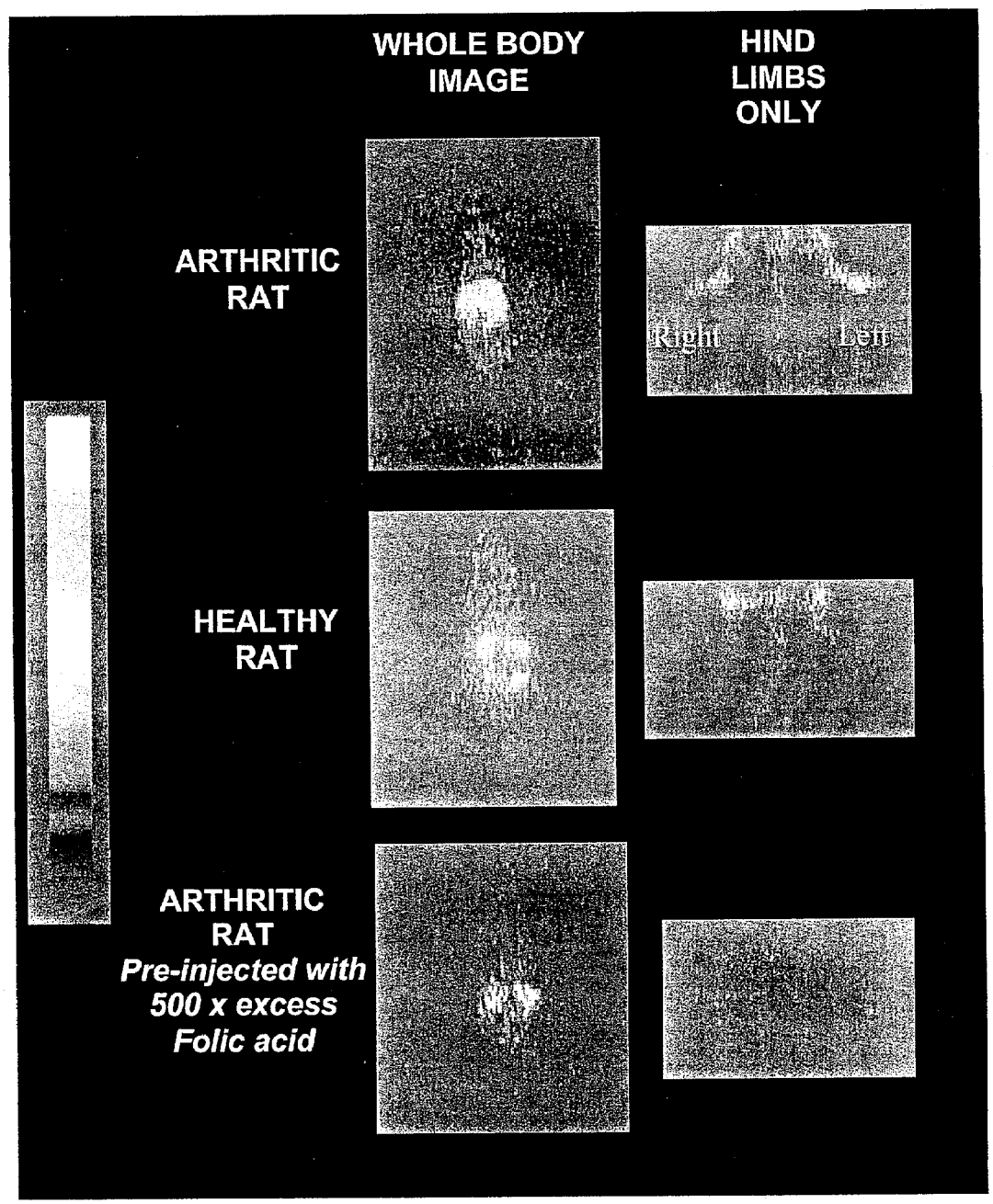
FIG. 1 shows folate-targeted imaging of arthritic rats (whole body scintigraphic images).

Methods are provided in accordance with the present invention for either treating or monitoring/diagnosing a disease state mediated by activated macrophages. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Such disease states can be monitored by first administering to a patient suffering from such disease state an effective amount of a composition comprising a conjugate of the general formula A$_b$-X wherein the group A$_b$ comprises a ligand capable of binding to activated macrophages, and the group X comprises an imaging agent and thereafter scanning the patient with an imaging device capable of detecting the imaging agent. Macrophage mediated disease states can be treated in accordance with this invention by administering an effective amount of a composition of the above formula wherein A$_b$ comprises a ligand capable of binding to an activated macrophage and wherein the group X comprises an immunogen, a cytotoxin, or a cytokine capable of altering macrophage function. Such macrophage targeting conjugates, when administered to a patient suffering from an activated macrophage mediated disease state, work to concentrate and associate the conjugated cytotoxin, immunogen, or cytokine with the population of activated macrophages to kill the activated macrophages or alter macrophage function. Elimination or deactivation of the activated macrophage population works to stop or reduce the activated macrophage mediated pathogenesis characteristic of the disease state being treated. The conjugate is typically administered parenterally as a composition comprising the conjugate and a pharmaceutically acceptable carrier therefor. Conjugate administration is typically continued until symptoms of the disease state are reduced or eliminated.

In one embodiment of the invention activated macrophage mediated disease states are monitored or diagnosed in a patient by administering a conjugate A$_b$-X wherein A$_b$ comprises a ligand capable of binding to activated macrophages and X comprises an imaging agent and thereafter scanning the patient with an imaging device capable of detecting localized concentration of the imaging agent. The imaging or diagnostic conjugates are, similar to those therapeutic conjugates outlined above, typically administered as a diagnostic composition comprising a conjugate and a pharmaceutically acceptable carrier. The composition is typically formulated for parenteral administration and is administered to the patient in an amount effective to enable imaging of the locale of activated macrophage populations. The nature of the imaging agent component of the conjugate is dictated by the imaging methodology. Thus, for example, the imaging agent can comprise a chelating moiety and a metal cation, for example, a radionuclide or a nuclear resonance imaging contrast agent, such as gadolinium. Typically the activated macrophage targeted imaging agent is administered to a patient, and following a period of time to allow delivery and concentration of the imaging agent in the activated macrophage cell populations, the patient is subjected to the imaging procedure and imaging is enabled by the targeted imaging agent.

The method of the present invention can be used for both human clinical medicine and veterinary applications. Thus, the host animals afflicted with the activated macrophage mediated disease state can be humans, or in the case of veterinary applications, they can be laboratory, agricultural, domestic or wild animals. The conjugates administered in accordance with the methods of this invention are preferably administered parenterally to the animal or patient suffering from the disease state, for example, intradermally, subcutaneously, intramuscularly, intraperitoneally, or intravenously. Alternatively, the conjugates can be administered to the animal or patient by other medically useful procedures and effective doses can be administered in standard or prolonged release dosage forms, such as a slow pump. The therapeutic method of the present invention may be used alone or in combination with other therapeutic methods recognized for the treatment of macrophage mediated disease states.

In the ligand conjugates of the general formula A$_b$-X in accordance with the present invention, the group A$_b$ is a ligand capable of binding to activated macrophages. Any of a wide number of macrophage binding moieties can be employed. Acceptable ligands include particularly folate receptor binding ligands and antibodies or antibody fragments capable of recognizing and specifically binding to surface moieties uniquely or preferentially expressed or presented in/on activated macrophages. In one embodiment the activated macrophage binding ligand is folic acid, a folic acid analog or other folate receptor binding molecules. Activated macrophages express a 38 LD GPI-anchored folate receptor that binds folate and folate-derivatized compounds with subnanomolar affinity (i.e., <1 nM). In another embodiment the activated macrophage binding ligand is a specific monoclonal or polyclonal antibody or Fab or scFv (i.e., a single chain variable region) fragments of antibodies capable of specific binding to activated macrophages.

The activated macrophage targeted conjugates used for diagnosing and monitoring disease states mediated by activated macrophages in accordance with this invention are formed to target and, thus, to concentrate an imaging agent at the site of activated macrophage populations in the diseased patient. In such conjugates of the formula A$_b$-X, A$_b$ is a ligand capable of binding to activated macrophages and the group X comprises an imaging agent. In one embodiment the imaging agent comprises a chelating agent and a metal cation, typically either a radionuclide or a nuclear magnetic resonance imaging enhancer or contrast agent, such as gadolinium. Such conjugates wherein the group A$_b$ is folic acid, a folic acid analog, or another folic acid receptor binding ligand are described in detail in U.S. Pat. No. 5,688,488, the specification of which is incorporated herein by reference. That patent, as well as related U.S. Pat. Nos. 5,416,016 and 5,108,921, each incorporated herein by reference, describe methods and examples for preparing chelate conjugates useful in accordance with the present invention. The present macrophage targeted imaging agents can be prepared and used following general protocols described in those earlier patents. The present diagnostic method, however, is based in part on the discovery that folate targeted conjugates can be used to concentrate conjugated imaging entities in and at activated macrophage populations enabling monitoring and diagnosis of disease states characterized by concentration of activated macrophages at the site of disease.

In accordance with one embodiment of the present invention there is provided a method of treating disease states mediated by activated macrophages by administering to a patient suffering from such disease state an effective amount of a composition comprising a conjugate of the general formula $A_b$-X wherein $A_b$ is as defined above and the group X comprises a cytotoxin, an immunogen, or a compound capable of altering macrophage function. Exemplary of cytotoxic moieties useful for forming conjugates for use in accordance with the present method include clodronate, anthrax, Pseudomonas exotoxin, typically modified so that these cytotoxic moieties do not bind to normal cells, and other toxins or cytotoxic agents including art-recognized chemotherapeutic agents such as adrenocorticoids, alkylating agents, antiandrogens, antiestrogens, androgens, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, cyclophosphamide, plant alkaloids, prednisone, hydroxyurea, teniposide, and bleomycin, nitrogen mustards, nitrosureas, vincristine, vinblastine, inflammatory and proinflammatory agents, and the like. Such toxins or cytotoxic components can be directly conjugated to the activated macrophage binding moiety, for example, folate or other folate receptor binding ligands, or they can be formulated in liposomes which themselves are targeted as conjugates of macrophage binding entities typically by covalent linkages to component phospholipids. Similarly, when the group X comprises a compound capable of altering a macrophage function, for example, a cytokine such as IL-10 or IL-11, the cytokine can be covalently linked to the targeting moiety $A_b$, for example, a folate receptor binding ligand or an antibody or antibody fragment directly, or the macrophage function altering cytokine can be encapsulated in a liposome which is itself targeted to activated macrophages by pendent macrophage targeting entities $A_b$ covalently linked to one or more phospholipid liposome components.

In another embodiment the ligand-immunogen conjugates can be administered in combination with a cytotoxic compound. The compounds listed in the preceding paragraph are among the compounds suitable for this purpose.

In another method of treatment embodiment of the present invention the group X in the activated macrophage targeted conjugate $A_b$-X, comprises an immunogen, the ligand-immunogen conjugates being effective to "label" the population of activated macrophages responsible for disease pathogenesis in the patient suffering from the disease for specific elimination by an endogenous immune response or by co-administered antibodies. The use of ligand-immunogen conjugates in the method of treatment in accordance with this invention works to enhance an immune response-mediated elimination of the activated macrophage population. Such can be effected through an endogenous immune response or by a passive immune response effected by co-administered antibodies. The endogenous immune response may include a humoral response, a cell-mediated immune response, and any other immune response endogenous to the host animal, including complement-mediated cell lysis, antibody-dependent cell-mediated cytotoxicity (ADCC), antibody opsonization leading to phagocytosis, clustering of receptors upon antibody binding resulting in signaling of apoptosis, antiproliferation, or differentiation, and direct immune cell recognition of the delivered antigen/hapten. It is also contemplated that the endogenous immune response will employ the secretion of cytokines that regulate such processes as the multiplication and migration of immune cells. The endogenous immune response may include the participation of such immune cell types as B cells, T cells, including helper and cytotoxic T cells, macrophages, natural killer cells, neutrophils, LAK cells, and the like.

In another embodiment, the ligand-immunogen conjugate can be internalized and the immunogen can be degraded and presented on the macrophage cell surface for recognition by immune cells to elicit an immune response directed against macrophages presenting the degraded immunogen.

The humoral response may be a response induced by such processes as normally scheduled vaccination, or active immunization with a natural antigen or an unnatural antigen or hapten, e.g., fluorescein isothiocyanate (FITC), with the unnatural antigen inducing a novel immunity. Active immunization involves multiple injections of the unnatural antigen or hapten scheduled outside of a normal vaccination regimen to induce the novel immunity. The humoral response may also result from an innate immunity where the host animal has a natural preexisting immunity, such as an immunity to α-galactosyl groups. Alternatively, a passive immunity may be established by administering antibodies to the host animal such as natural antibodies collected from serum or monoclonal antibodies that may or may not be genetically engineered antibodies, including humanized antibodies. The utilization of a particular amount of an antibody reagent to develop a passive immunity, and the use of a ligand-immunogen conjugate wherein the passively administered antibodies are directed to the immunogen, would provide the advantage of a standard set of reagents to be used in cases where a patient's preexisting antibody titer to other potential antigens is not therapeutically useful. The passively administered antibodies may be "co-administered" with the ligand-immunogen conjugate, and co-administration is defined as administration of antibodies at a time prior to, at the same time as, or at a time following administration of the ligand-immunogen conjugate. It is contemplated that the preexisting antibodies, induced antibodies, or passively administered antibodies will be redirected to the activated macrophages by preferential binding of the ligand-immunogen conjugates to the activated macrophage cell populations, and such pathogenic cells are killed by complement-mediated lysis, ADCC, antibody-dependent phagocytosis, or antibody clustering of receptors. The cytotoxic process may also involve other types of immune responses, such as cell-mediated immunity, as well as secondary responses that arise when the attracted antigen-presenting cells phagocytose the activated macrophages and present antigens of such cells to the immune system for elimination of other activated macrophages presenting such antigens.

Acceptable immunogens for use in preparing the conjugates used in the method of treatment of the present invention are immunogens that are capable of eliciting antibody production in a host animal or that have previously elicited antibody production in a host animal, resulting in a preexisting immunity, or that constitute part of the innate immune system. Alternatively, antibodies directed against the immunogen may be administered to the host animal to establish a passive immunity. Suitable immunogens for use in the invention include antigens or antigenic peptides against which a preexisting immunity has developed via normally scheduled vaccinations or prior natural exposure to such agents such as polio virus, tetanus, typhus, rubella, measles, mumps, pertussis, tuberculosis and influenza antigens and α-galactosyl groups. In such cases, the ligand-immunogen conjugates will be used to redirect a previously acquired humoral or cellular immunity to a population of activated macrophages in the host animal for elimination of such cells. Other suitable immunogens include antigens or antigenic peptides to which the host animal has developed a novel immunity through immunization against an unnatural antigen or hapten, for example, fluorescein isothiocyanate (FITC) or dinitrophenyl and antigens against which an innate immunity exists, for example, super antigens and muramyl dipeptide. It is also contemplated that MHC I restricted peptides could be linked to the ligand for use in redirecting cellular immunity to macrophages and eliciting T cell killing of macrophages.

The macrophage binding ligands and immunogens, cytotoxic agents, cytokines or imaging agents, as the case may be in forming conjugates for use in accordance with the present invention, may be conjugated by using any art-recognized method for forming a complex. This can include covalent, ionic, or hydrogen bonding of the ligand to the immunogen, either directly or indirectly via a linking group such as a divalent linker. The conjugate is typically formed by covalent bonding of the ligand to the targeted entity through the formation of amide, ester or imino bonds between acid, aldehyde, hydroxy, amino, or hydrazo groups on the respective components of the complex. Alternatively, as mentioned above, the ligand complex can be one comprising a liposome wherein the targeted entity (that is, the imaging agent, or the immunogen, cytotoxic agent or macrophage function altering agent) is contained within a liposome which is itself covalently linked to the activated macrophage binding ligand.

In one embodiment of the invention the ligand is folic acid, an analog of folic acid, or any other folate receptor binding molecule, and the folate ligand is conjugated to the targeted entity by a procedure that utilizes trifluoroacetic anhydride to prepare γ-esters of folic acid via a pteroyl azide intermediate. This procedure results in the synthesis of a folate ligand, conjugated to the targeted entity only through the γ-carboxy group of the glutamic acid groups of folate. Alternatively, folic acid analogs can be coupled through the α-carboxy moiety of the glutamic acid group or both the α and γ carboxylic acid entities.

Additional folate receptor binding ligands include folinic acid, pteropolyglutamic acid, and folate receptor-binding pteridines such as tetrahydropterins, dihydrofolates, tetrahydrofolates, and their deaza and dideaza analogs are preferred complex-forming ligands used in accordance with a second embodiment of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid derivatives are conventionally termed "folates," reflecting their capacity to bind with folate receptors, and such ligands when complexed with exogenous molecules are effective to enhance transmembrane transport. Other folates useful as complex forming ligands for this invention are the folate receptor-binding analogs aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate).

The conjugates used in accordance with this invention of the formula $A_b$-X are used in one aspect of this invention to formulate therapeutic or diagnostic compositions comprising effective amounts of the conjugate and an acceptable carrier therefor. Typically such compositions are formulated for parenteral use. The amount of the conjugate effective for use in accordance with the invention depends on many parameters, including the nature of the disease being treated or diagnosed, the molecular weight of the conjugate, its route of administration and its tissue distribution, and the possibility of co-usage of other therapeutic or diagnostic agents. The effective amount to be administered to a patient is typically based on body surface area, patient weight and physician assessment of patient condition. An effective amount can range from about to 1 ng/kg to about 1 mg/kg, more typically from about 1 μg/kg to about 500 μg/kg, and most typically from about 1 μg/kg to about 100 μg/kg.

When used for monitoring or diagnosis, imaging procedures are typically carried out about 1 to about 6 hours post administration of the activated macrophage targeted imaging agent.

Any effective regimen for administering the ligand conjugates can be used. For example, the ligand conjugates can be administered as single doses, or they can be divided and administered as a multiple-dose daily regimen. Further, a staggered regimen, for example, one to three days per week can be used as an alternative to daily treatment, and for the purpose of defining this invention such an intermittent or staggered daily regimen is considered to be equivalent to every day treatment and within the scope of this invention. In one embodiment of the invention the patient is treated with multiple injections of the ligand conjugate wherein the targeted entity is an immunogen or a cytotoxic agent to eliminate the population of pathogenic activated macrophages. In one embodiment, the patient is treated, for example, injected multiple times with the ligand conjugate at, for example, at 12-72 hour intervals or at 48-72 hour intervals. Additional injections of the ligand conjugate can be administered to the patient at intervals of days or months after the initial injections, and the additional injections prevent recurrence of disease. Alternatively, the ligand conjugates may be administered prophylactically to prevent the occurrence of disease in patients known to be disposed to development of activated macrophage mediated disease states. In one embodiment of the invention more than one type of ligand conjugate can be used, for example, the host animal may be pre-immunized with fluorescein isothiocyanate and dinitrophenyl and subsequently treated with fluorescein isothiocyanate and dinitrophenyl linked to the same or different activated macrophage targeting ligands in a co-dosing protocol.

The ligand conjugates are administered in accordance with this invention parenterally and most typically by intraperitoneal injections, subcutaneous injections, intramuscular injections, intravenous injections or intrathecal injections. The ligand conjugates can also be delivered to a patient using an osmotic pump. Examples of parenteral dosage forms include aqueous solutions of the conjugate, for example, solution in isotonic saline, 5% glucose or other well-known pharmaceutically acceptable liquid carriers such as alcohols, glycols, esters and amides. The parenteral compositions for use in accordance with this invention can be in the form of a reconstitutable lyophilizate comprising the one or more doses of the ligand conjugate. In another aspect of the invention, the ligand conjugates can be formulated as one of any of a number of prolonged release dosage forms known in the art such as, for example, the biodegradable carbohydrate matrices described in U.S. Pat. Nos. 4,713,249; 5,266,333; and 5,417,982, the disclosures of which are incorporated herein by reference.

EXAMPLE 1

Materials

EC20 (a folate-linked chelator $^{99m}$Tc), EC28 (the same $^{99m}$Tc chelate complex without folate), and folate-fluorescein isothiocyanate (folate-FITC) were gifts from Endocyte, Inc. (West Lafayette, Ind.). Heat-killed *Mycoplasma butericum* was purchased from BD Biosciences (Sparks, Md.). Folic acid, light mineral oil, clodronate, collagenase-A, and streptavidin-R-phycoerythrin were obtained from Sigma Chemical Co. (St. Louis, Mo.), and Dubelco's Modified Eagle Medium (DMEM) was from Gibco-BRL (Gathersburg, Md.). $^3$H-folic acid was obtained from American Radiolabeled Chemicals, Inc. (St. Louis, Mo.) and Microcon®-30 membranes were purchased from Millipore Corp. (Bedford, Mass.). RK-4-biotin and ED2-R-phycoerythrin antibodies were acquired from Bachem Biosciences, Inc. (Philadelphia, Pa.) and Accurate Chemical and Scientific Corp. (Westbury, N.Y.), respectively.

EXAMPLE 2

Animal Model of Arthritis

Arthritis was induced in 150-200 g female Lewis rats (Charles River Laboratories, Inc., Wilmington, Mass.), n=4/dose group. Briefly, 0.5 mg of heat-killed *Mycoplasma butericum*, suspended in mineral oil (5 mg/ml), was injected on day 0 into the left hind foot of rats following anesthesia with ketamine and xylazine. Disease was allowed to progress for 21 days, and animals were weighed on a daily basis to ensure the status of their health. All treated animals developed arthritis, as evidenced by dramatic swelling in the injected paw, progressive swelling in all noninjected limbs due to the systemic progression of arthritis, and radiographic analysis of affected limbs. All rats were maintained on a folate-deficient diet (DYETS, Inc., Bethlehem, Pa.) for 3 weeks prior to administration of folate-FITC in order to lower serum folate levels to physiologically relevant concentrations. Control rats were also maintained on a folate-deficient diet but not induced to develop arthritis.

EXAMPLE 3

Elimination of Endogenous Macrophages

Evaluation of macrophage independent uptake of the folate-linked imaging agent was accomplished by killing endogenous macrophages with liposomal clodronate. Liposomes were formed by rehydrating a thin film of egg phosphatidylcholine (60 mole %) and cholesterol (40 mole %) in an isotonic clodronate solution (250 mg/ml). Small unilamellar vesicles were then generated by extrusion of the liposomes ten times through a 100 nm polycarbonate membrane using a 10 ml thermobarrel extruder (Lipex Biomembranes, Vancouver, Canada). Unencapsulated clodronate was removed by dialysis through a Spectrapor 300,000 $M_r$-cutoff cellulose acetate membrane (Spectrum Laboratories, Rancho Domingues, Calif.), and the clodronate concentration in the retained liposomes was determined as described in *J. Microencapsul.* 3(2) 109-14 (1986). Seventeen days following induction of the arthritis and three days prior to administration of the imaging agent (EC20), rats destined for macrophage depletion received a single intraperitoneal injection of clodronate liposomes containing 20 mg clodronate.

EXAMPLE 4

Scintigraphy and Biodistribution Analysis

Twelve hours prior to administration of imaging agent, all animals received 5 ml of normal saline subcutaneously to ensure proper excretion of unbound imaging agent. Twenty-one days following induction of arthritis, rats (n=3 per group) were injected intraperitoneally with 500 µCi (2.3 nmoles/rat) of either EC20 (folate+chelator), EC20+500-fold molar excess folic acid, or EC28 (no folate moiety). Four hours later, rats underwent either nuclear scintigraphic imaging or biodistribution analysis.

For scintigraphy, rats were anesthetized with ketamine and xylazine, and positioned in ventral recumbency on the image acquisition surface. Image acquisition was performed for one minute at a count rate of 50-75,000 counts per minute using a Technicare Omega 500 Sigma 410 Radioisotope Gamma Camera. Following acquisition of whole body images, radiation of the upper body (above the stifles) was blocked using ⅛" lead plates, and images of the posterior limbs were obtained. All data were analyzed using a Medasys™ MS-DOS-based computer equipped with Medasys™ Pinnacle software.

For biodistribution analysis, rats were euthanized by intraperitoneal injection of nebutal or pentobarbitol sodium. Liver, spleen, heart, lungs, intestine, and kidneys were then harvested and radiation in each tissue was determined by counting in a gamma counter (Packard BioScience Co., Meridian, Conn.).

EXAMPLE 5

Assay of Tissue Folate Receptor Levels

Folate receptor levels in each tissue were determined follows. Briefly, tissues were homogenized and cell membranes were isolated by centrifugation. Membrane proteins were solubilized overnight, transferred into a Microcon®-30 filtration device, and incubated with 50 nM $^3$H-folic acid. A duplicate of each sample, used to determine non-specific binding, was also exposed to 50 nM $^3$H-folic acid, but in the presence of 1000-fold excess unlabeled folic acid. After unbound $^3$H-folic acid was washed through the membrane, membrane protein with bound $^3$H-folic acid was recovered and counted in a scintillation counter (Packard BioScience Co.) to determine the number of active folate receptors per gram of tissue.

EXAMPLE 6

Identification of the Folate Receptor Expressing Cell Type in Liver

Arthritic and healthy rats were first anesthetized with ketamine and xylazine, and then a midline incision was made, starting in the lower abdomen and extending through the thoracic cavity. A 24-gauge catheter was inserted into the hepatic vein, and a 24-gauge needle was inserted in the cardiac left ventricle to serve as an outlet for the perfusion fluid. Rats were then perfused by delivery of normal saline, followed by collagenase A solution (0.05% in Gey's balanced salt solution) through the catheter. Each solution was perfused for two minutes at a rate of 20 ml/minute. Immediately after perfusion, livers were removed and the membranous outer tissue was dissected away. The remaining gelatinous tissue was suspended in collagenase-A solution (0.025% in DMEM) and incubated at 37° C. for two hours in the presence of 1 µM folate-FITC or 1 µM folate-FITC+1 mM folic acid. Cells were then washed three times to removed unbound folate-FITC and immediately prepared for flow cytometry.

EXAMPLE 7

Flow Cytometry Sample Preparation and Analysis

Liver cell preparations, which had been exposed to folate-FITC, were treated for 10 mm at 4° C. with ammonium chloride lysis buffer (150 mM NH$_4$Cl, 10 mM KHCO$_3$, 1 mM EDTA, pH 7.4) to lyse red blood cells. Following three washes with phosphate buffered saline, the remaining cells were incubated for 1 h at 4° C. with either ED2 R-Phycoerythrin-labeled mouse anti-rat macrophage antibody, or RK-4 biotin-labeled mouse-anti rat granulocyte antibody. Cells were again washed two times, and those that had received the biotinylated primary antibody were further incubated with streptavidin-R-Phycoerythrin for 30 minutes. Following two final washes, cells were examined for FITC and phycoerythrin dual color staining on a FACScan Coulter XL flow cytometer.

EXAMPLE 8

Immunotherapy Mediated Protection Against Adjuvant-Induced Arthritis

Figure 9:
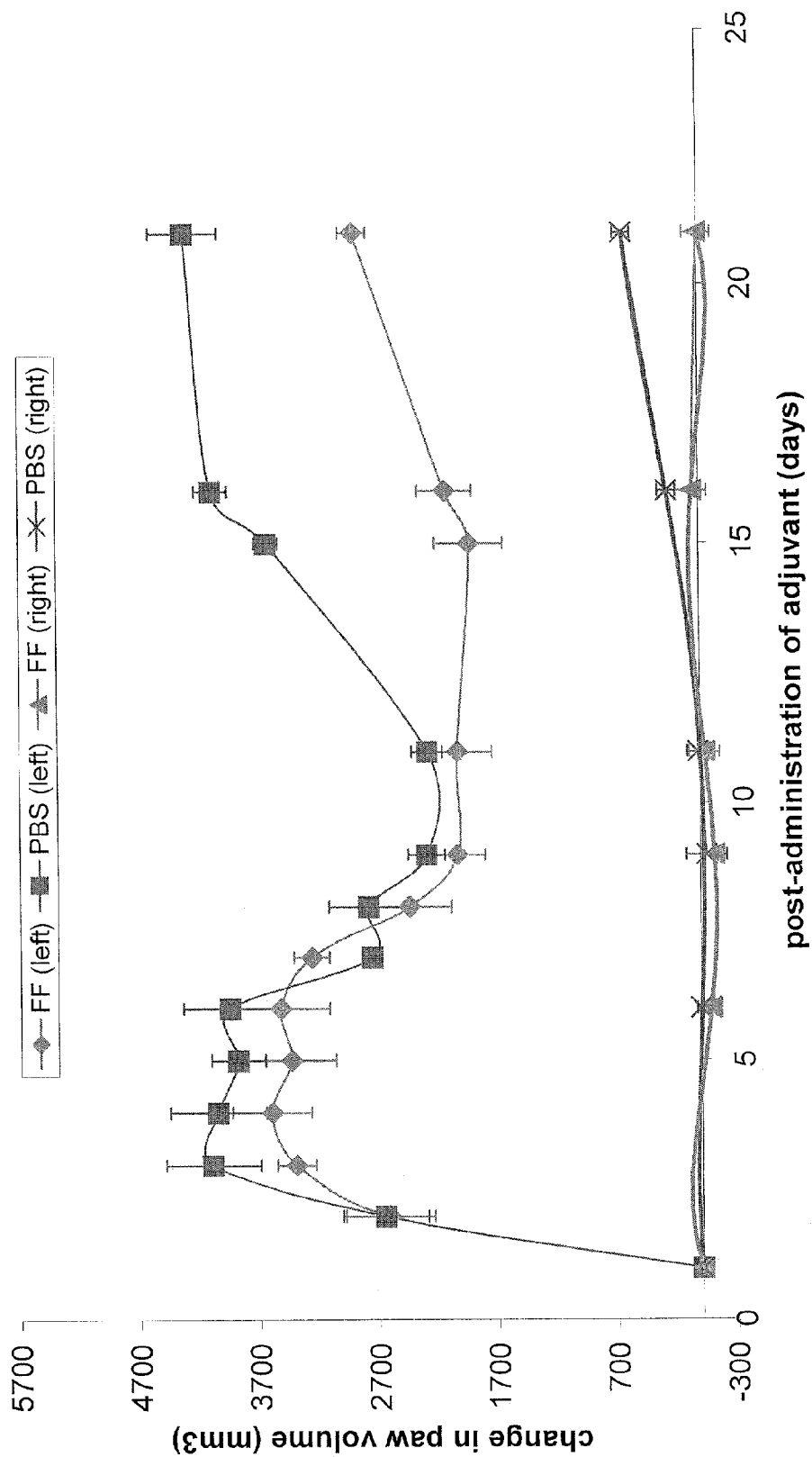
FIG. 9 demonstrates immunotherapy mediated protection against adjuvant-induced arthritis (diamonds represent folate-FITC (left foot), squares represent PBS (left foot), triangles represent folate-FITC (right foot), and X's represent PBS (right foot)).

The protocol described in Example 2 for arthritis induction was followed. The efficacy of a folate-FITC conjugate (folate-fluorescein isothiocyanate conjugate) against adjuvant-induced arthritis in rats was investigated. Each rat used in the experiment was immunized at the base of the tail with FITC-KLH (150 µg) to induce antibodies against FITC on days −38 and −10 before administration of *Mycoplasma butericum* (adjuvant) to induce arthritis. The immunization of FITC-KLH was done in combination with an adjuvant (i.e., such as TITERMAX® GOLD (150 µg), Alum (150 µg), or GPI-100 (150 µg) which are all adjuvants to induce antibodies against FITC as opposed to the adjuvant used to induce arthritis). The immunized animals were then injected on day 0 in the left foot pad with 0.5 mg of heat-killed *Mycoplasma butyricum* (adjuvant) to initiate development of arthritis. Then on days 1, 2, 3, 9, 11, and 14, post-adjuvant (*Mycoplasma butyricum*) injection, the rats were injected intraperitoneally with either saline (control rats) or 2000 nmoles/kg of folate-FITC (FF). Calipers were used to measure left and right foot dimensions daily. With reference to FIG. 9, those measurements are plotted for both the adjuvant-injected feet (top two curves) and the non-treated feet (bottom two curves). A sudden increase in swelling of the adjuvant-injected feet is due to influx of neutrophils which have no folate receptors. Consequently, the immunotherapy has no impact on this phase of paw swelling. However, after about 10 days, activated macrophages invade both injected feet and uninjected feet, causing bone degradation and further inflammation. These activated macrophages have functional folate receptors, and, as shown, they are eliminated or reduced by binding folate-hapten conjugates such as folate-FITC.

EXAMPLE 9

Folate-Targeted Imaging of Arthritic Rats

Figure 8:
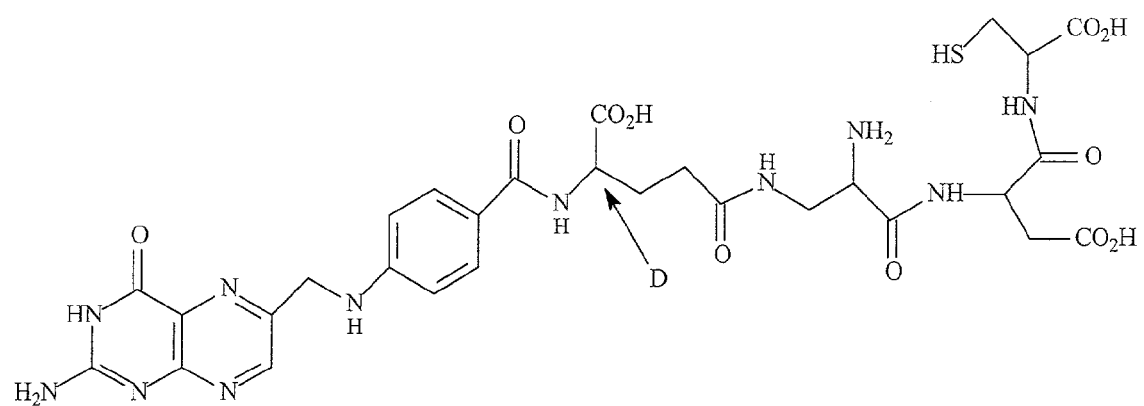
FIG. 8 shows a chemical structure representing the folate-linked chelator EC20.

The protocols described in Examples 2 and 4 were followed. As noted above, activated but not resting macrophages express a receptor for the vitamin folic acid. To determine whether folate might be exploited to target $^{99m}$Tc to sites of arthritic inflammation, EC20, a folate-linked chelator of $^{99m}$Tc (see FIG. 8) was administered intraperitoneally to rats (n=5/group) and scintigraphic images were acquired with a gamma camera. Due to the rapid clearance of EC20, excellent contrast was obtained by at least four hours post-administration (FIG. 1). Importantly, whole body uptake was significantly more intense in arthritic rats compared to healthy rats, and this uptake was greatly reduced when EC20 was administered together with a saturating dose of free folic acid. This suggests that uptake by all tissues is primarily determined by a folic-specific receptor.

Intense organ uptake of EC20 prevented visualization of limbs in whole body images of the arthritic rats. However, images of posterior limbs could be easily acquired when mid and upper body radiation was shielded. With such shielding, arthritic limbs displayed much greater EC20 uptake than healthy extremities, and this uptake was completely eliminated in the presence of excess free folic acid (FIG. 1). Furthermore, the left rear foot of the arthritic animals, where inflammation was most severe, displayed greater uptake than the less severely affected right rear foot (FIG. 1).

Figure 2:
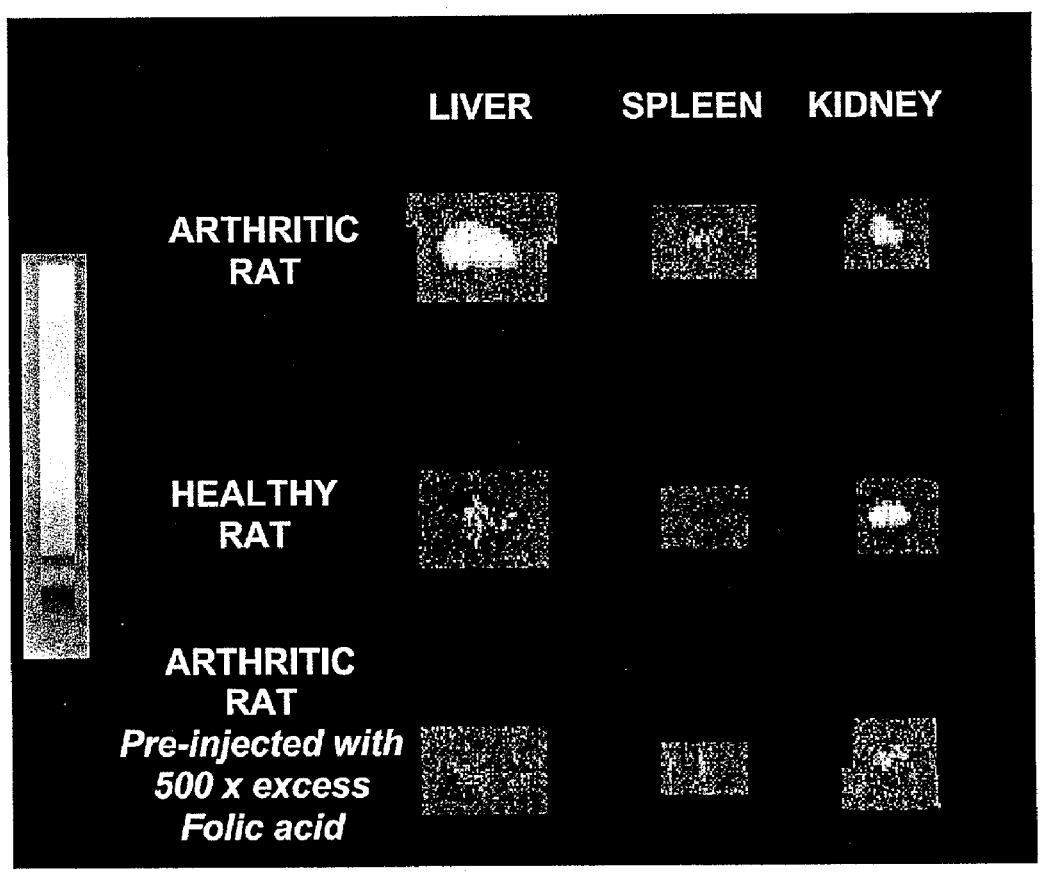
FIG. 2 shows folate-targeted imaging of arthritic rats (assessment of liver, spleen and kidney by scintigraphy).

From the whole body images, it could be concluded that abdominal organs were responsible for a majority of EC20 uptake in the arthritic animals. To confirm this assessment, liver, spleen and kidney were removed and imaged separately (FIG. 2). Livers of arthritic rats demonstrated the highest uptake of EC20, while livers of healthy rats displayed minimal uptake. Only those spleens taken from arthritic rats could be visualized. Free folic acid completely blocked EC20 uptake in liver and spleen, however, the free vitamin only partially decreased uptake by the kidney.

EXAMPLE 10

Effects of Macrophage Depletion

Figure 3:
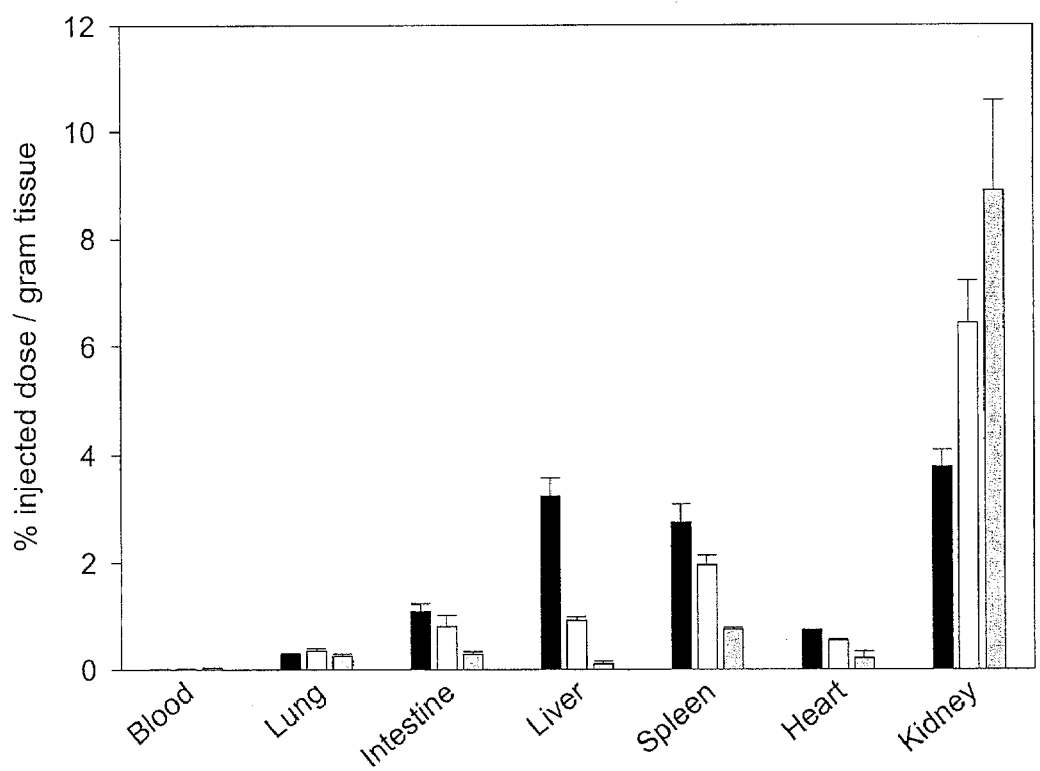
FIG. 3 shows effects of macrophage depletion (black bars represent arthritic rats, light gray bars represent healthy rats, and dark gray bars represent arthritic rats depleted of macrophages by clodronate treatment).

The protocols described in Examples 2, 3, and 4 were followed, except that 0.25 mCi of EC20 was administered. In order to determine whether macrophages might be responsible for the uptake of EC20, resident macrophages were systemically eliminated from arthritic rats using a liposomal clodronate preparation (n=3 rats/group). By four days after clodronate treatment, evaluation of paw size revealed that clodronate-treated rats were significantly less inflamed than untreated rats (data not shown). To determine whether macrophage elimination would influence uptake of the folate-linked imaging agent, EC20 biodistribution analysis was then performed on the clodronate-treated rats and compared to the same analysis of both healthy rats and arthritic rats not treated with clodronate. As shown in FIG. 3 (black bars represent arthritic rats, light gray bars represent healthy rats, and dark gray bars represent arthritic rats depleted of macrophages by clodronate treatment), depletion of macrophages decreased liver uptake of EC20 ~20-fold in arthritic rats, while retention in the spleen and intestine was reduced by a factor of three. In most tissues, clodronate treatment depressed EC20 uptake even below those levels observed in healthy rats, confirming the hypothesis that activated macrophages account for most of EC20 retention in normal tissues. In contrast, kidney uptake of EC20 was elevated in rats depleted of macrophages, most likely because the decreased internalization of EC20 by activated macrophages rendered more EC20 available for binding to kidney folate receptors.

EXAMPLE 11

Folate Receptor-Mediated Uptake of EC20 in Arthritic Tissues

Figure 4:
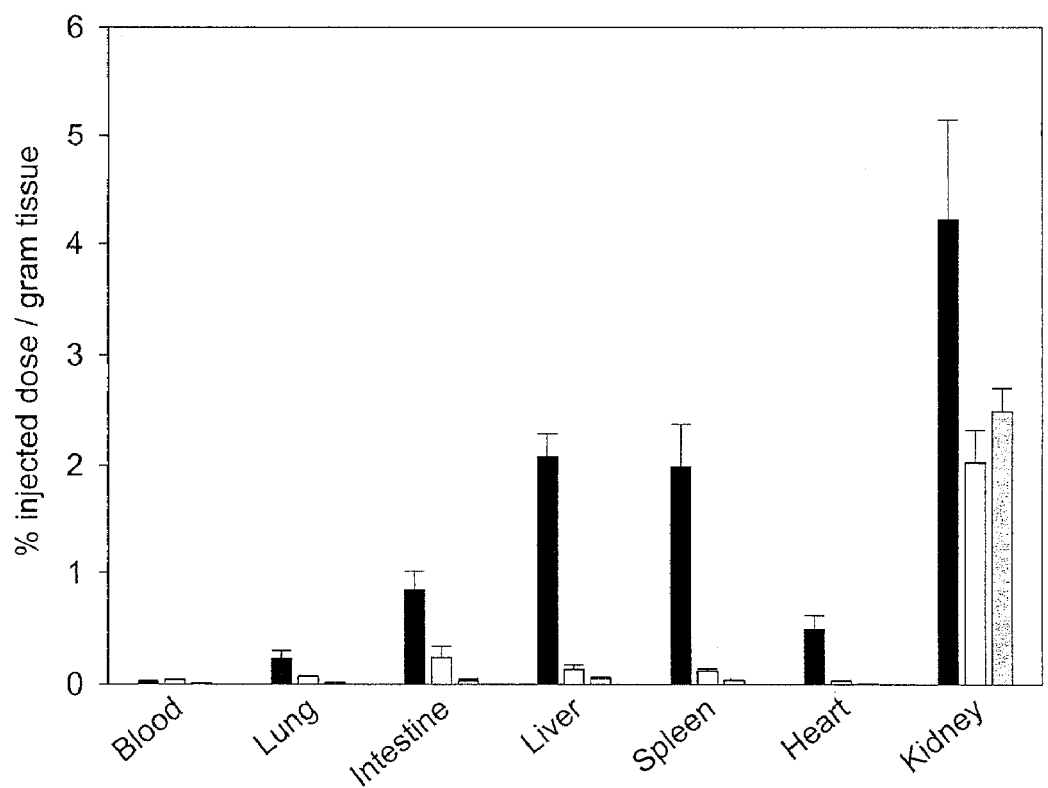
FIG. 4 shows folate receptor-mediated uptake of EC20 in arthritic tissues (light gray bars represent biodistribution of EC20 in the presence of a 500-fold excess of free folic acid, black bars represent biodistribution of EC20 in the absence of a 500-fold excess of free folic acid, dark gray bars represent the biodistribution of the same complex lacking a folate moiety (EC28)).

The protocols described in Examples 2 and 4 were followed. Two additional biodistribution studies were conducted to confirm that EC20 uptake by tissues of arthritic rats is mediated by the folate receptor (n=3 rats/group). First, the biodistribution of EC20 was examined in the presence (light gray bars) and absence (black bars) of a 500-fold excess of free folic acid. As seen in FIG. 4, almost complete elimination of EC20 uptake was observed in all tissues except kidney, indicating that binding was indeed mediated by a folate receptor. In fact, excess folic acid competitively reduced EC20 retention in liver, spleen, heart, lung, intestine and blood to near background levels (FIG. 4). Second, to confirm the role of folate in EC20-mediated targeting of the chelated $^{99m}$Tc, the biodistribution of the same complex lacking a folate moiety (EC28) was also examined (dark gray bars). As also displayed in FIG. 4, uptake of EC28 was negligible in all tissues except kidney, where retention of the non-targeted complex was similar to that of EC20 in the presence of competing folic acid.

EXAMPLE 12

Folate Receptor Expression in Various Tissues of Arthritic Rats

Figure 5:
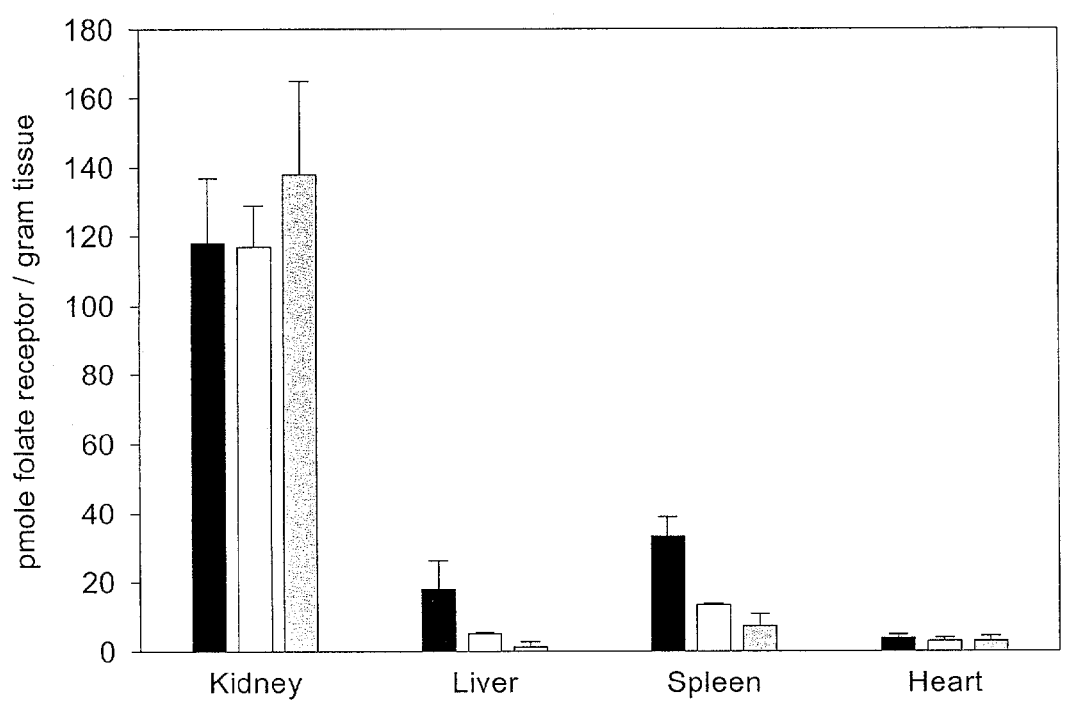
FIG. 5 shows folate receptor expression in various tissues of arthritic rats (black bars represent arthritic rats, light gray bars represent healthy rats, and dark gray bars represent arthritic rats depleted of macrophages by clodronate treatment).

The protocols described in Examples 2, 4, and 5 were used. The above results suggest that the folate receptor is responsible for tissue uptake of EC20. In order to confirm this, Applicants attempted to directly quantitate the folate binding protein in various rat tissues. Active folate receptor could be detected in each of the major organs examined, and FR levels were significantly increased in arthritic rats (FIG. 5; black bars=arthritic rats; light gray bars=healthy rats). Further, FR content correlated well with uptake of EC20 seen in the biodistribution studies. In fact, the FR assay revealed roughly equivalent levels of receptor in arthritic liver and spleen, in accordance with the similar uptake of EC20 by the same organs (FIG. 4). Significantly, systemic elimination of macrophages by clodronate treatment (dark gray bars) lowered folate receptor levels in all arthritic tissues (FIG. 5), also in good agreement with the EC20 biodistribution analysis. Finally, the FR assay confirmed that neither induction of arthritis nor clodronate treatment alters the levels of FR in kidney or heart, where FR is not thought to be associated with activated macrophages.

EXAMPLE 13

Figure 6:
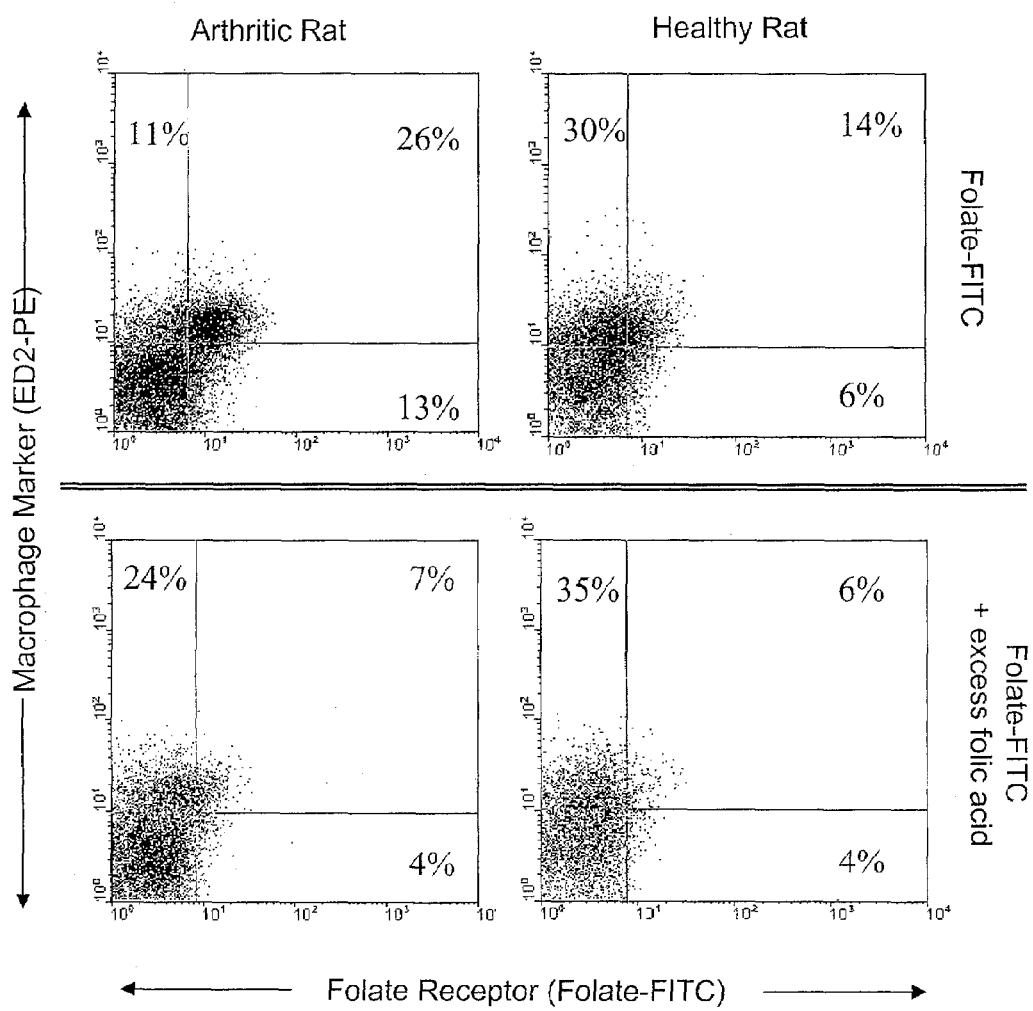
FIG. 6 shows expression of a functional folate receptor on liver macrophages of arthritic rats.

Expression of a Functional Folate Receptor on Liver Macrophages of Arthritic Rats The protocols described in Examples 2, 4, 6 and 7 were used. To further confirm that the elevated uptake of EC20 in livers of arthritic rats is due to a macrophage population, livers were resected from collagenase-perfused rats and their disaggregated cells examined for folate conjugate uptake, using folate-FITC as a fluorescent marker for FR expression. By also labeling the same liver cell suspension with an antibody specific for rat liver macrophages, it was possible to demonstrate that macrophages are indeed the cell type that expresses elevated levels of folate receptor in arthritic animals (FIG. 6). Thus, flow cytometric analysis revealed that 70% of the liver macrophages of arthritic rats bound folate-FITC compared to only 30% of the liver macrophages of healthy rats (FIG. 6). Further, the FITC intensity of the arthritic macrophages was higher than that of macrophages from healthy livers. Since binding of folate-FITC was suppressed in the presence of an excess of free folic acid (1 mM), we concluded that uptake of the folate conjugate by liver macrophages was mediated by the folate receptor.

Using an antibody specific for granulocytes, we also examined whether tissue infiltrating neutrophils might take up folate conjugates. Although very few neutrophils were found in the liver, those that were detected exhibited no binding capacity for folate-FITC (data not shown). Mac-1+ peripheral blood cells were also tested and similarly found to have no binding affinity for the folate-conjugate (data not shown). In fact, no peripheral blood cells sorted positive for FITC fluorescence, suggesting that only resident tissue macrophages (and clearly only a subpopulation of those) express FR in the liver.

Figure 7:
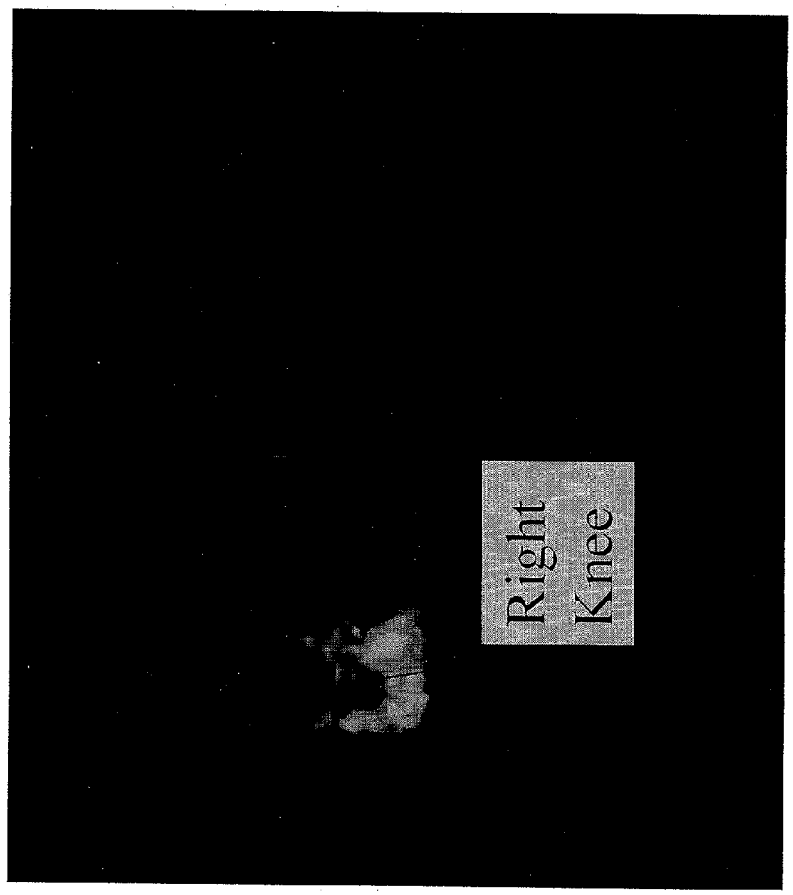
FIG. 7 shows increased uptake of a folate-targeted imaging agent in a patient with an inflamed joint.

Finally, to begin to explore whether activated macrophages might be targeted with folate-linked drugs in human patients, we obtained permission to examine the whole body images of the 28 suspected ovarian cancer patients enrolled in a recently completed clinical trial of the gamma imaging agent, $^{111}$In-DTPA-Folate. As shown in FIG. 7, one patient displayed significant imaging agent uptake in the right knee, but not the left knee. Importantly, no other patients demonstrated any measurable joint uptake. Upon request, the attending physician contacted the anonymous patient and inquired whether she had been experiencing any chronic joint discomfort. The physician responded that the patient reported arthritis in the right knee.

Discussion

Activated macrophages are thought to be intimately involved in the pathogenesis of rheumatoid arthritis. Activated macrophages directly destroy joint tissue by secreting metalloproteinases and attracting/activating other immune cells by releasing cytokines. The quantitation of activated macrophages in joint tissues might be of diagnostic value, since activated macrophage content correlates well with articular destruction and poor disease prognosis in humans.

Gamma camera scintigraphy of rats receiving EC20 demonstrated that arthritic appendages are indeed illuminated by folate-targeted $^{99m}$Tc. In contrast, the legs and feet of healthy rats could not be visualized, demonstrating the selectivity of the imaging agent for arthritis applications. Although the intensities of internal organs also increased in adjuvant-induced arthritis, interference from such tissues did not appear to compromise the methodology, since gamma radiation from internal, organs could be easily screened. The fact that excellent contrast can be obtained within one to two hours of EC20 injection further shows that imaging agent administration, gamma camera scintigraphy, and image analysis can be completed during the same examination.

Systemic activation of macrophages has been documented in rats with adjuvant-induced arthritis. Thus, it was important to establish the specific participation of macrophages in the elevated uptake of EC20, since a folate-targeted imaging agent had never previously been examined in arthritic animals. Three experiments were conducted for this purpose. First, clodronate-loaded liposomes were employed to systemically deplete macrophages from the treated rats. Not only were the resulting tissue FR levels greatly reduced, but uptake of EC20 in the macrophage-rich organs was also nearly eliminated, suggesting that resident macrophages can indeed account for both FR expression and EC20 retention in the RES organs. Second, liver cells were disaggregated by collagenase treatment and individual cells were evaluated for folate conjugate uptake. As noted in FIG. 6, the vast majority of cells testing positive for folate conjugate uptake also sorted positive for the macrophage marker, ED2, confirming that FR is indeed present on the macrophages. Finally, because other immune and myelocytic cells are known to be elevated in tissues of rats with adjuvant-induced arthritis, it was conceivable that still another extravasating blood cell type might be involved in the uptake of EC20. However, neither liver-infiltrating granulocytes nor any blood cell in circulation displayed any capacity to bind folate-FITC. Thus, activated macrophages would seem to be the predominant cell type internalizing folate conjugates in the organs of arthritic rats.

It was surprising to find that up to 30% of the liver macrophages in healthy rats also expressed the folate receptor (FIG. 6). Since a functional folate receptor is not found on resting synovial macrophages, it is tempting to speculate that the folate-FITC binding fraction in the healthy rats might also constitute an activated population. Two observations may support this conjecture. First, activated macrophages are also found in healthy tissues following exposure to immune stimulants such as foreign antigens. Given the role of the liver in clearing foreign substances from the body, a low level of resident macrophage activation does not seem unreasonable. Second, the folate-FITC (and EC20) binding population of liver cells increased significantly upon induction of localized inflammation and systemic macrophage activation.

With the ability to exploit folate to deliver attached molecules to activated macrophages now established, folate-linked imaging agents will allow the early development or continued progression of rheumatoid arthritis to be assessed. Since graft versus host disease, multiple sclerosis, Crohn's disease, ulcerative colitis, psoriasis, osteomyelitis, and even atherosclerosis may also be caused/aggravated by activated macrophages, it is possible that the diagnosis/evaluation of these diseases could be aided by a folate-linked imaging/contrast agent. The avid folate conjugate uptake by activated macrophages in both arthritic joints and liver indicates that macrophages can be effectively targeted regardless of their anatomical location.

EXAMPLE 14

Immunotherapy Mediated Protection Against Adjuvant-Induced Arthritis

Figure 10:
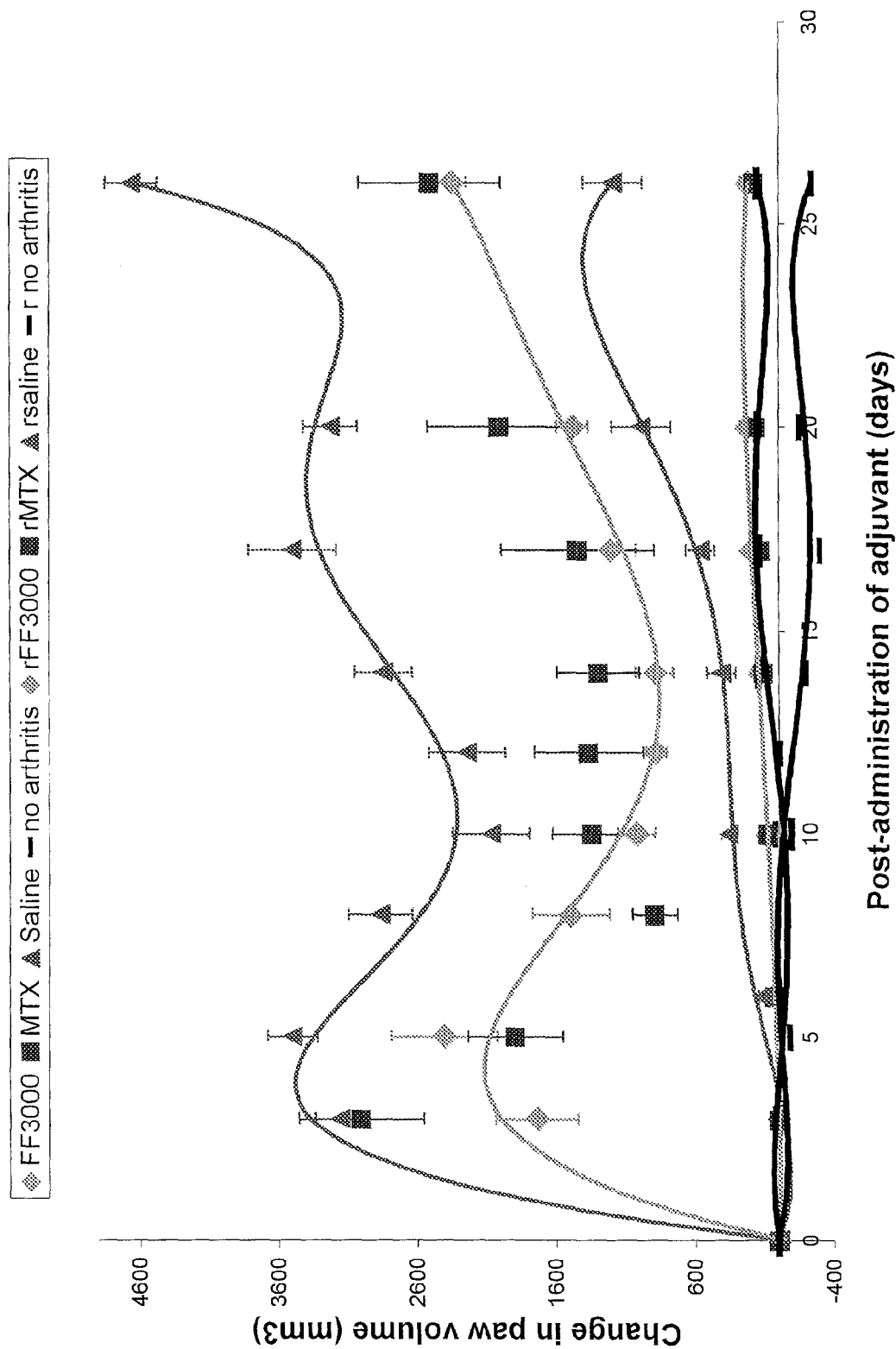
FIG. 10 demonstrates immunotherapy mediated protection against adjuvant-induced arthritis (light gray diamonds represent administration of folate-FITC, dark gray squares represent administration of methotrexate, dark gray triangles represent administration of saline, and black lines represent animals without arthritis). The bottom four lines represent the uninjected paw.

For the assay shown in FIG. 10, the protocol described in Example 8 was followed except that 3000 nmoles/kg of folate-FITC was administered per day (3 doses on days 1, 2, and 3) and folate-FITC was delivered using an osmotic pump implanted into the peritoneal cavity of the rat. Methotrexate (MTX) was administered at a dose of 0.15 mg by intraperitoneal injection one time per day on days 1, 8, and 15 after adjuvant administration. MTX was used in place of folate-FITC for animals treated with MTX. The results for both the left (injected) and right (uninjected) paw are shown. The results show that folate-FITC (FF) inhibits adjuvant-induced arthritis as well as MTX.

EXAMPLE 15

Immunotherapy Mediated Protection Against Adjuvant-Induced Arthritis

Figure 11:
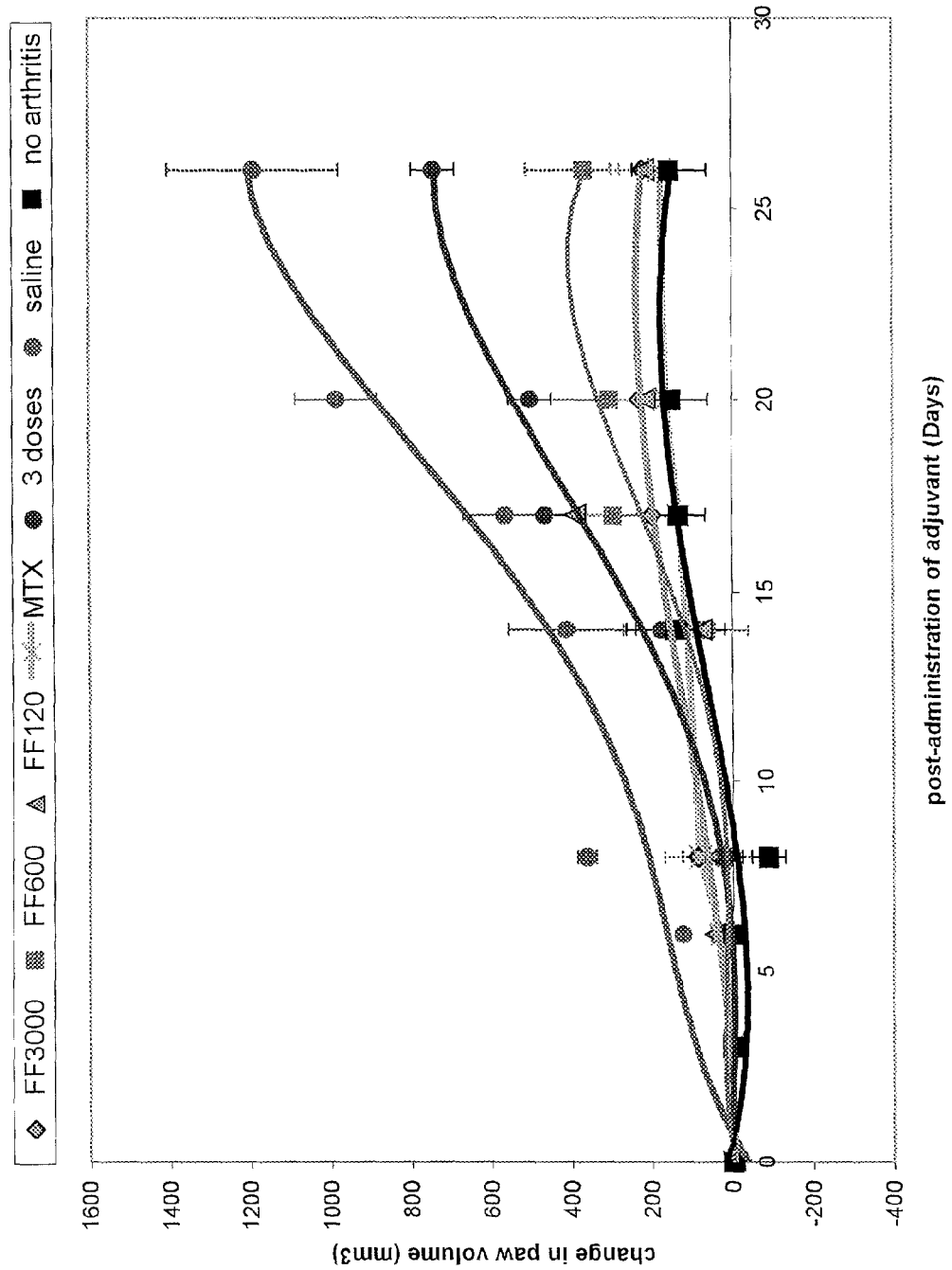
FIG. 11 demonstrates immunotherapy mediated protection against adjuvant-induced arthritis in the right (uninjected) paw (light gray diamonds represent administration of folate-FITC at 3000 nmoles/kg, light gray squares represent administration of folate-FITC at 600 nmoles/kg, light gray triangles represent administration of folate-FITC at 120 nmoles/kg, light gray X's represent administration of methotrexate, dark gray circles represent administration in 3 doses (as in Example 14), light gray circles represent administration of saline, and black squares represent animals without arthritis).

The protocol described in Example 14 was followed except that only the right paw volume was measured and folate-FITC (FF) was administered at doses of 3000, 600, and 120 nmoles/kg (FIG. 11). Also, FF was administered at 3000 nmoles/kg in either three doses as in Example 14 (indicated as "3 doses" in FIG. 11) or on days 1, 2, 3, 9, 11, and 14 as described in Example 8 (indicated as "FF3000" in FIG. 11). The results show that FF inhibits adjuvant-induced arthritis in the right paw of the arthritic rats (inflammation presumably appears in the uninjected right paw due to the systemic progression of arthritis), and that prolonged treatment with FF is more effective than 3 initial doses for treatment of adjuvant-induced arthritis.

EXAMPLE 16

Immunotherapy Mediated Protection Against Adjuvant-Induced Arthritis

Figure 12:
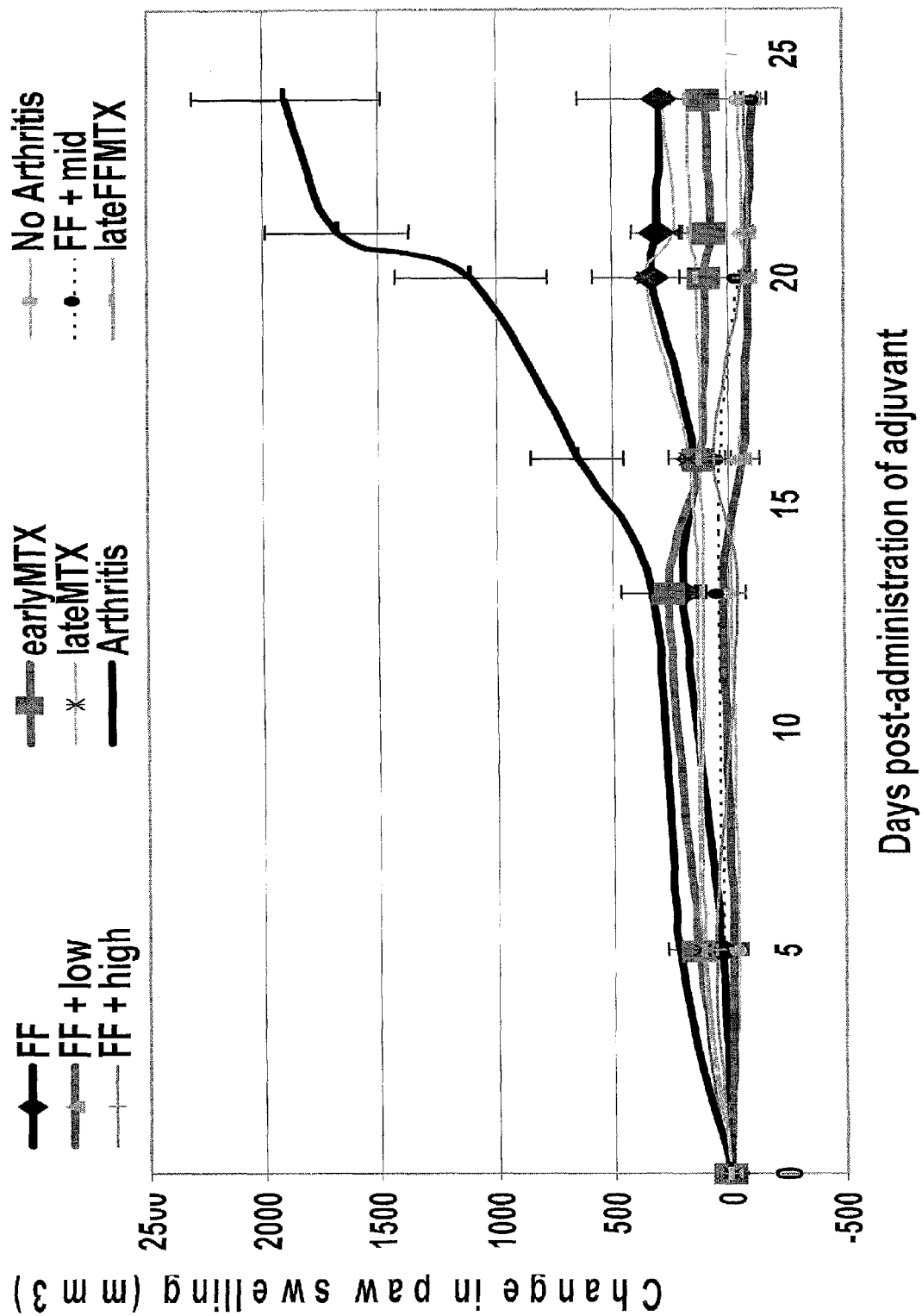
FIG. 12 demonstrates immunotherapy mediated protection against adjuvant-induced arthritis (black diamonds=FF, gray triangles=FF+low, vertical hash marks=FF+high, gray squares=early MTX, gray X's=late MTX, thick black lines=arthritis, gray circles=no arthritis, black circles=FF+mid, horizontal hash marks=late FFMTX).

The protocol described in Example 8 was followed except MTX was used at a dose of 0.15 mg (FF+low, early MTX, late MTX and lateFFMTX) to treat some animals in place of FF (see FIG. 12). Other animals were treated with 0.75 mg of MTX (FF+mid) or 1.5 mg of MTX (FF+high). For "early MTX" treatments, the rats were injected with MTX on days 1, 8, and 15 after arthritis induction. For "late MTX" treatments, the rats were injected with MTX on days 8 and 15 after adjuvant administration. All measurements were of the uninjected right paw. The results show that folate-FITC (FF) in combination with MTX (early or late treatments and a low, high, or middle dose of MTX) inhibits adjuvant-induced arthritis better than FF alone.

EXAMPLE 17

Immunotherapy Mediated Protection Against Adjuvant-Induced Arthritis

Figure 13:
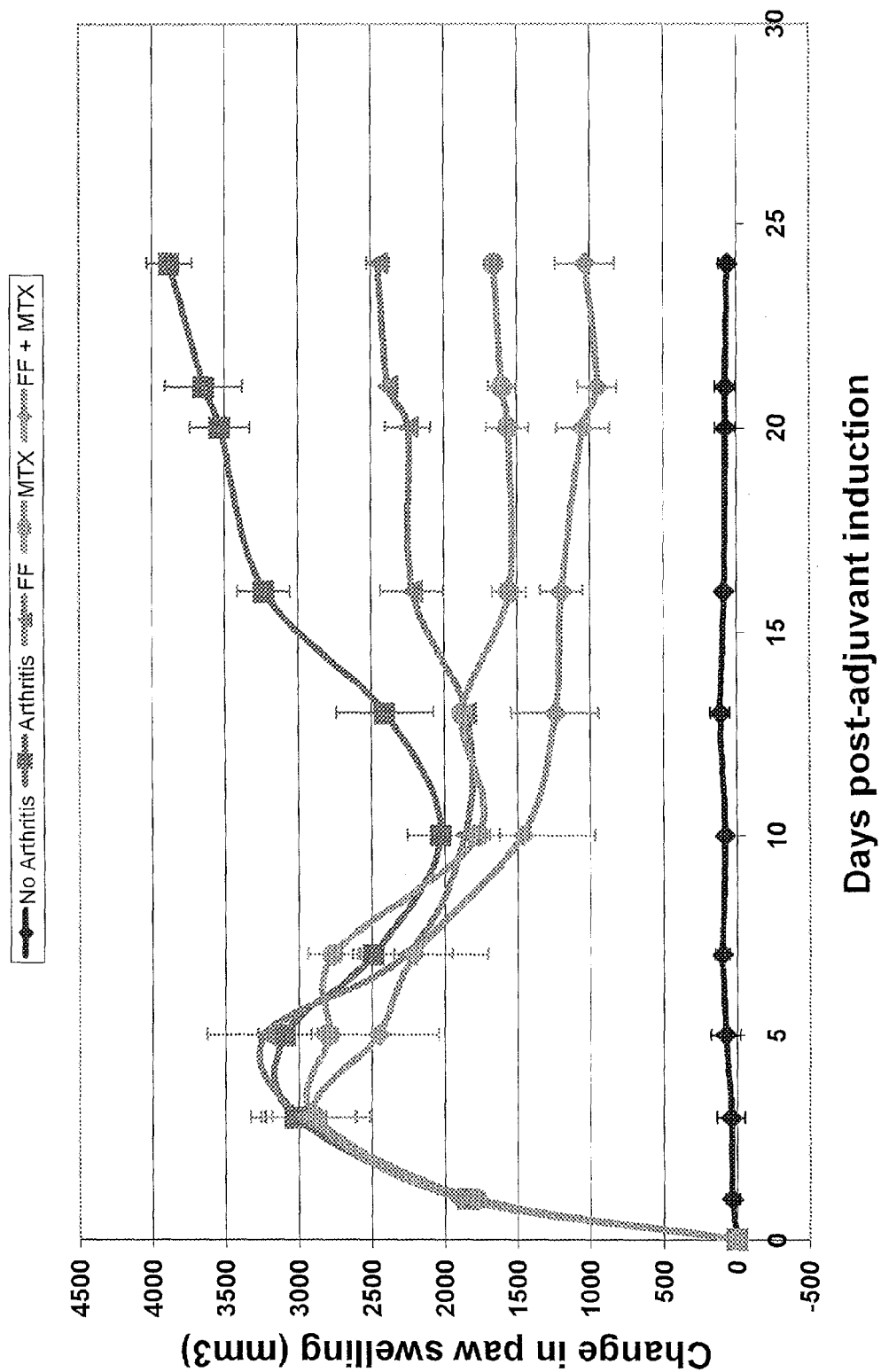
FIG. 13 demonstrates immunotherapy mediated protection against adjuvant-induced arthritis (black diamonds represent animals with no arthritis, dark gray squares represent animals with arthritis, light gray triangles represent administration of folate-FITC, light gray circles represent administration of methotrexate, and light gray diamonds represent administration of the combination of folate-FITC and methotrexate).

For the results shown in FIG. 13, the protocol described in Example 8 was followed except that some animals were treated with MTX alone (0.15 mg) on days 1, 8, and 15 after arthritis induction or were treated with MTX (0.15 mg; days 1, 8, and 15) in combination with FF as described in Example 14. The results show that the combination of FF and MTX inhibits adjuvant-induced arthritis to a greater extent than MTX or FF alone.

EXAMPLE 18

Immunotherapy Mediated Protection Against Adjuvant-Induced Arthritis

Figure 14:
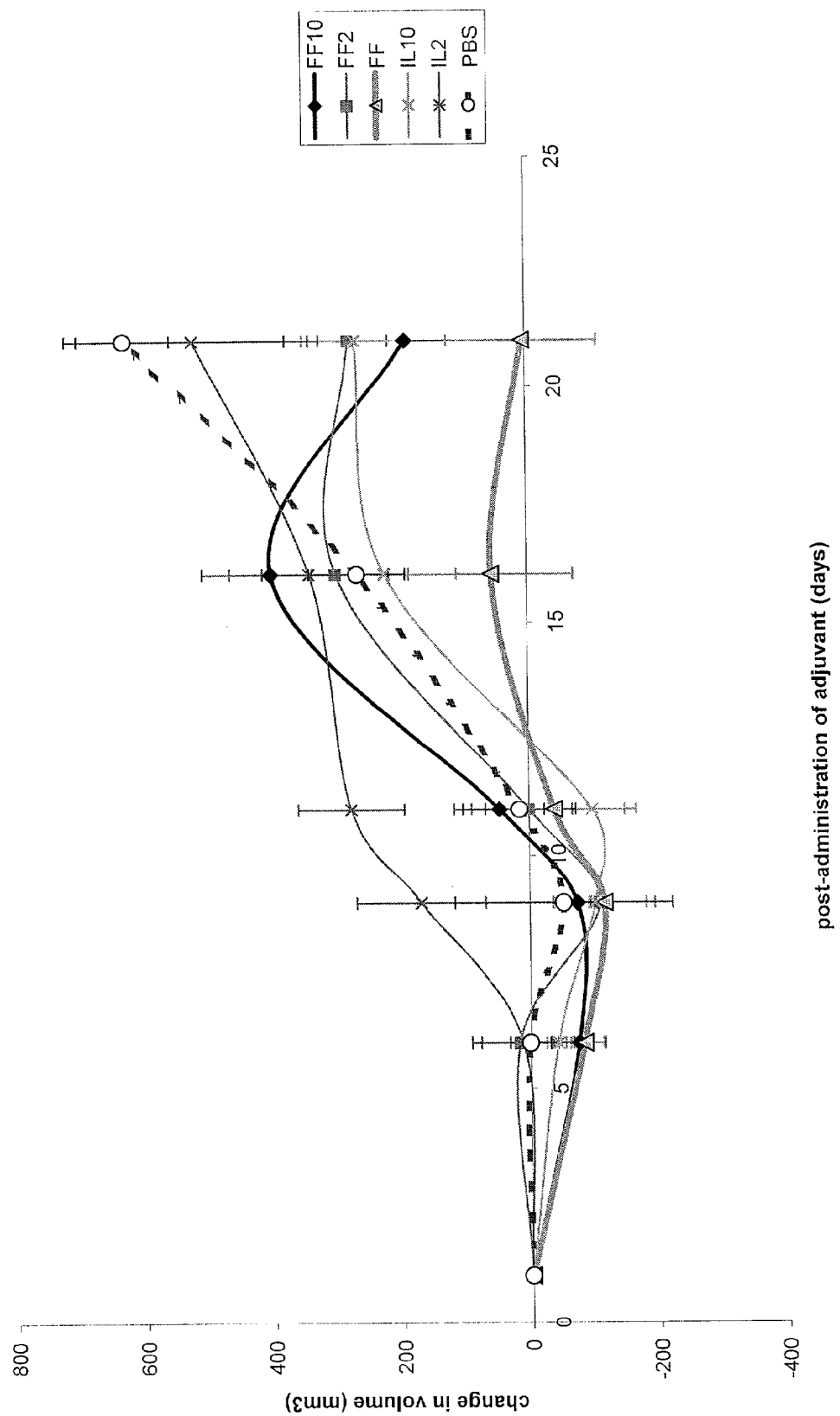
FIG. 14 demonstrates immunotherapy mediated protection against adjuvant-induced arthritis (black diamonds=FF10, gray squares=FF2, gray triangles=FF, gray X's=IL10, black X's=IL2, open circles=PBS).

The protocol described in Example 8 was followed except that IL-10 (10,000 U; FF10) or IL-2 (3 μg/kg; FF2) was administered along with the treatments with FF (i.e., the cytokines were administered by intraperitoneal injections on days 1, 2, 3, 9, 11, and 14 after adjuvant administration; see FIG. 14). The measurements made were measurements of the right, noninjected paw. The results show that either IL-10 or IL-2 prevent the inhibition of adjuvant-induced arthritis resulting from treatment with FF. All of the above immunotherapy results taken together indicate that folate-linked agents which are cytotoxic for macrophages can be used to treat macrophage-mediated disease states.

EXAMPLE 19

Folate-Targeted Imaging of Arthritic Rats

Figure 15:
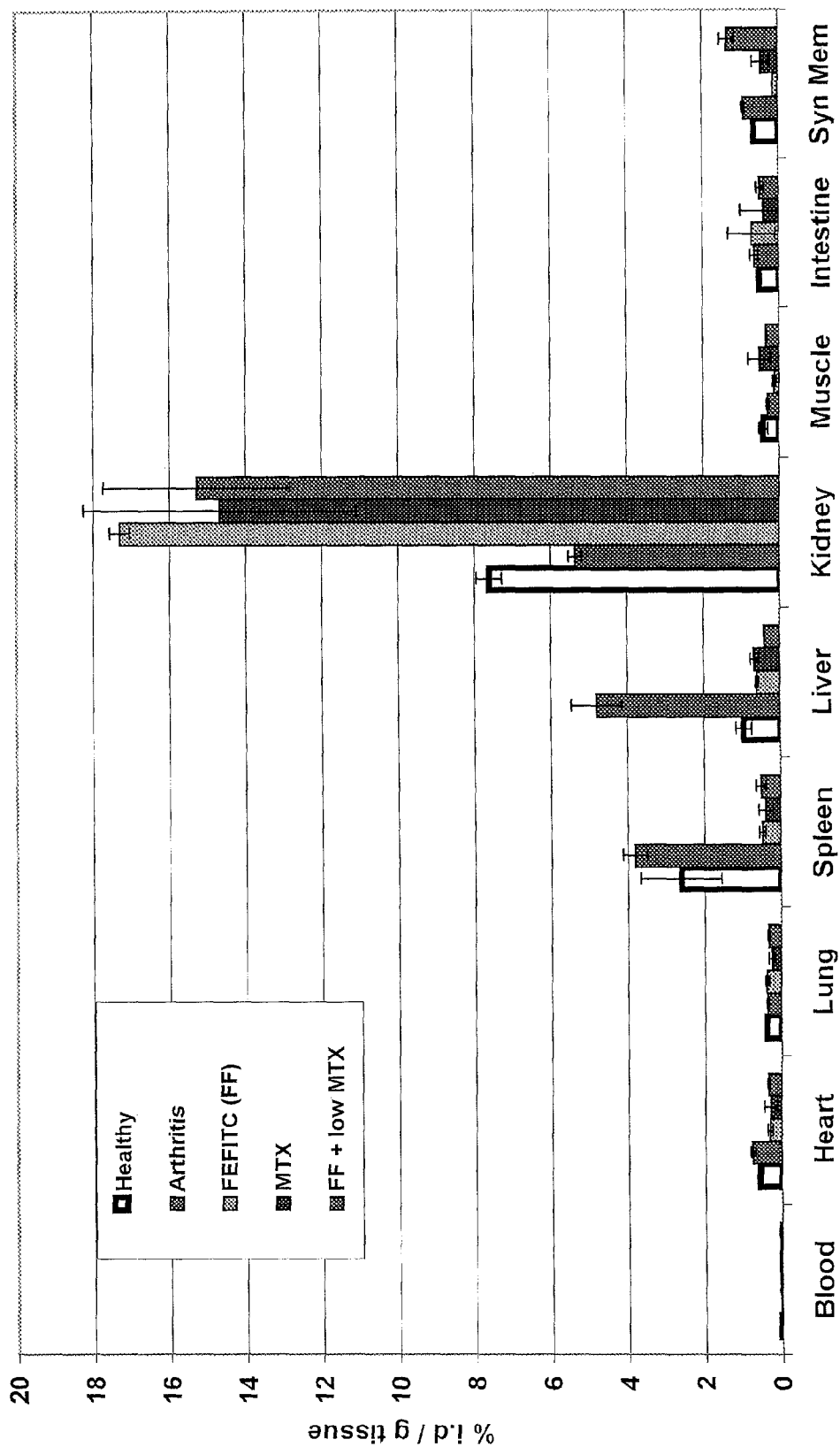
FIG. 15 shows folate-targeted imaging of arthritic rats (1$^{st}$ bar=Healthy, 2$^{nd}$ bar=Arthritis, 3$^{rd}$ bar=FEFITC (FF), 4$^{th}$ bar=MTX, 5$^{th}$ bar=FF+low MTX). The organs are shown on the X-axis.

For the assay shown in FIG. 15, the protocols were as described in Examples 2 and 4 except that some animals were treated with FF (2000 nmoles/kg; days 1, 2, 3, 9, 11, and 14) or MTX (0.15 mg; days 1, 8, and 15) as described in Examples 8 and 14, respectively. The results show that FF or MTX prevent EC20 uptake in all organs examined except the kidney. It is likely that EC20 uptake is reduced in most organs making more EC20 available for excretion through the kidney accounting for the increase in EC20 detected in kidney tissues.

The invention claimed is:

1. A method of treating a disease state selected from the group consisting of arthritis, ulcerative colitis, atherosclerosis, and lupus erythematosus, said method comprising the step of administering to a patient suffering from the disease state an effective amount of a composition comprising a conjugate or complex of the general formula $A_b$-X where the group $A_b$ comprises folate, wherein folate binds to the folate receptor and wherein the group X comprises fluorescein isothiocyanate and wherein the conjugate or complex is administered to elicit an antibody response in the patient.

2. The method of claim 1 wherein the disease state is arthritis.

3. The method of claim 1 wherein the disease state is ulcerative colitis.

4. The method of claim 1 wherein the disease state is lupus erythematosus.

5. A method of treating a disease state mediated by activated macrophages selected from the group consisting of arthritis, ulcerative colitis, atherosclerosis, and lupus erythematosus, said method comprising the step of, administering to a patient suffering from the macrophage mediated disease state an effective amount of a composition comprising a conjugate or complex of the general formula $A_b$-X where the group $A_b$ comprises folate, wherein the folate binds to the folate receptor and is capable of binding to the activated macrophages and the group X comprises a hapten selected from the group consisting of a fluorescein and a polynitrophenyl; and wherein the conjugate or complex is administered to elicit an antibody response in the patient.

6. The method of claim 5 wherein the hapten is selected from the group consisting of fluorescein isothiocyanate and dinitrophenyl.

7. The method of claim 6 wherein the disease state is arthritis.

8. The method of claim 6 wherein the disease state is ulcerative colitis.

9. The method of claim 6 wherein the disease state is lupus erythematosus.

10. The method of claim 6 wherein the disease state is atherosclerosis.

11. The method of claim 1 wherein the disease state is atherosclerosis.

12. The method of claim 5 further comprising the step of administering an adjuvant to the patient.

13. The method of claim 5 wherein the disease state is arthritis.

14. The method of claim 5 wherein the disease state is ulcerative colitis.

15. The method of claim 5 wherein the disease state is lupus erythematosus.

16. The method of claim 5 wherein the disease state is atherosclerosis.

17. The method of claim 5 wherein the polynitrophenyl is selected from the group consisting of dinitrophenyls and trinitrophenyls.

* * * * *